(12) United States Patent
Van Duinen et al.

(10) Patent No.: US 11,529,659 B2
(45) Date of Patent: Dec. 20, 2022

(54) METHOD FOR REMOTE CONTROL OF DECONTAMINATION OF MEDICAL WASTE

(71) Applicant: Bluestone Medical, Inc., Newport Beach, CA (US)

(72) Inventors: Roger Van Duinen, Newport Beach, CA (US); Brad Barnes, Laguna Beach, CA (US); Kenneth Galer, Wake Forest, NC (US); Dennis Lambe, Salem, MA (US)

(73) Assignee: Bluestone Medical, Inc., Newport Beach, CA (US)

( * ) Notice: Subject to any disclaimer, the term of this patent is extended or adjusted under 35 U.S.C. 154(b) by 302 days.

(21) Appl. No.: 17/061,431

(22) Filed: Oct. 1, 2020

(65) Prior Publication Data

US 2022/0105550 A1    Apr. 7, 2022

(51) Int. Cl.
| | |
|---|---|
| *B09B 3/00* | (2022.01) |
| *A61L 11/00* | (2006.01) |
| *G05B 19/042* | (2006.01) |
| *B09B 3/40* | (2022.01) |

(52) U.S. Cl.
CPC .............. *B09B 3/0075* (2013.01); *A61L 11/00* (2013.01); *B09B 3/40* (2022.01); *G05B 19/042* (2013.01); *G05B 2219/2644* (2013.01)

(58) Field of Classification Search
CPC ........... B09B 3/00; B09B 3/0075; B09B 3/40; A61L 11/00; G05B 19/042; G05B 2219/2644

USPC ........................................................ 588/321
See application file for complete search history.

(56) References Cited

U.S. PATENT DOCUMENTS

| | | |
|---|---|---|
| 5,605,245 A | 2/1997 | Bemis et al. |
| 5,972,291 A | 10/1999 | Healy et al. |
| 8,011,507 B2 | 9/2011 | Anderson et al. |

OTHER PUBLICATIONS

The TE-5000 Onsite Waste Technology https://vimeo.com/332095512, 1 page.

*Primary Examiner* — Edward M Johnson
(74) *Attorney, Agent, or Firm* — Foley & Lardner LLP

(57) ABSTRACT

A method for remote control of decontamination of medical waste in an apparatus includes receiving, by a server via a first network interface and from the apparatus via a second network interface, a plurality of signals, the plurality of signals comprising operation data of the apparatus generated while the apparatus performs medical waste decontamination cycles in a first configuration; analyzing, by the server, the plurality of signals according to an operation policy; selecting, by the server, a first signal based on the analyzing the plurality of signals; and adjusting, by the server, operation of the apparatus by transmitting, via the first network interface, instructions to the second network interface of the apparatus, the instructions comprising the first signal, wherein receipt of the instructions causes the apparatus to perform a medical waste decontamination cycle in a second configuration different from the first configuration.

15 Claims, 14 Drawing Sheets

METHOD FOR REMOTE CONTROL OF DECONTAMINATION OF MEDICAL WASTE

BACKGROUND

The following description is provided to assist the understanding of the reader. None of the information provided or references cited is admitted to be prior art.

The safe handling and disposal of regulated medical waste from various medical and healthcare facilities is a well-known problem. Such medical healthcare facilities often need to safely dispose of contaminated scalpels, needles, and/or sharp metal or glass objects that are used during medical procedures. These items may include thermoplastic materials that are not easily disposed of.

However, medical facilities often need to comply with local environmental regulations that restrict them from disposing of medical waste in a conventional manner (e.g., by sending it to a landfill). In some instances, the medical facilities may use a local apparatus to decontaminate the medical waste before disposing of it. The local apparatus may be configured to run decontamination cycles when a user inserts medical waste into the apparatus. Such apparatuses often experience errors during these cycles that can cause the medical waste to remain contaminated and the process to be non-compliant with local environmental regulations. Consequently, users are often forced to transmit medical waste to remote facilities for further processing.

SUMMARY

In accordance with at least some aspects, the present disclosure discloses a method for remote control of decontamination of medical waste in an apparatus. The method includes: receiving, by a server via a first network interface and from the apparatus via a second network interface, a plurality of signals, the plurality of signals comprising operation data of the apparatus generated while the apparatus performs medical waste decontamination cycles in a first configuration; analyzing, by the server, the plurality of signals according to an operation policy; selecting, by the server, a first signal based on the analyzing the plurality of signals; and adjusting, by the server, operation of the apparatus by transmitting, via the first network interface, instructions to the second network interface of the apparatus, the instructions comprising the first signal, wherein receipt of the instructions causes the apparatus to perform a medical waste decontamination cycle in a second configuration different from the first configuration.

In accordance with other aspects, the present disclosure discloses A system for remote control of decontamination of medical waste in an apparatus, the system comprising a server comprising a processor having programmed instructions that, when executed, cause the processor to receive, via a first network interface and from the apparatus via a second network interface, a plurality of signals, the plurality of signals comprising operation data of the apparatus while the apparatus performs medical waste decontamination cycles in a first configuration; analyze the plurality of signals according to an operation policy; select a first signal based on the analyzing the plurality of signals; and adjust operation of the apparatus by transmitting, via the first network interface, instructions to the second network interface of the apparatus, the instructions comprising the first signal, wherein receipt of the instructions causes the apparatus to perform a medical waste decontamination cycle in a second configuration different from the first configuration.

In accordance with yet other aspects, the present disclosure discloses a method for remote control of decontamination of medical waste in an apparatus. The method includes transmitting, by the apparatus via a first network interface and to a server via a second network interface, a plurality of signals, the plurality of signals comprising operation data of the apparatus generated while the apparatus performs medical waste decontamination cycles in a first configuration, transmission of the plurality of signals causing the server to analyze the plurality of signals according to an operation policy; select a first signal based on the analyzing the plurality of signals; and adjust operation of the apparatus by transmitting, via the second network interface, instructions to the first network interface of the apparatus, the instructions comprising the first signal; and responsive to receiving the instructions comprising the first signal, performing a medical waste decontamination cycle in a second configuration different from the first configuration.

The foregoing summary is illustrative only and is not intended to be in any way limiting. In addition to the illustrative aspects, embodiments, and features described above, further aspects, embodiments, and features will become apparent by reference to the following drawings and the detailed description.

BRIEF DESCRIPTION OF THE DRAWINGS

The details of one or more implementations are set forth in the accompanying drawings and the description below. Other features, aspects, and advantages of the disclosure will become apparent from the description, the drawings, and the claims, in which:

Figure 1:
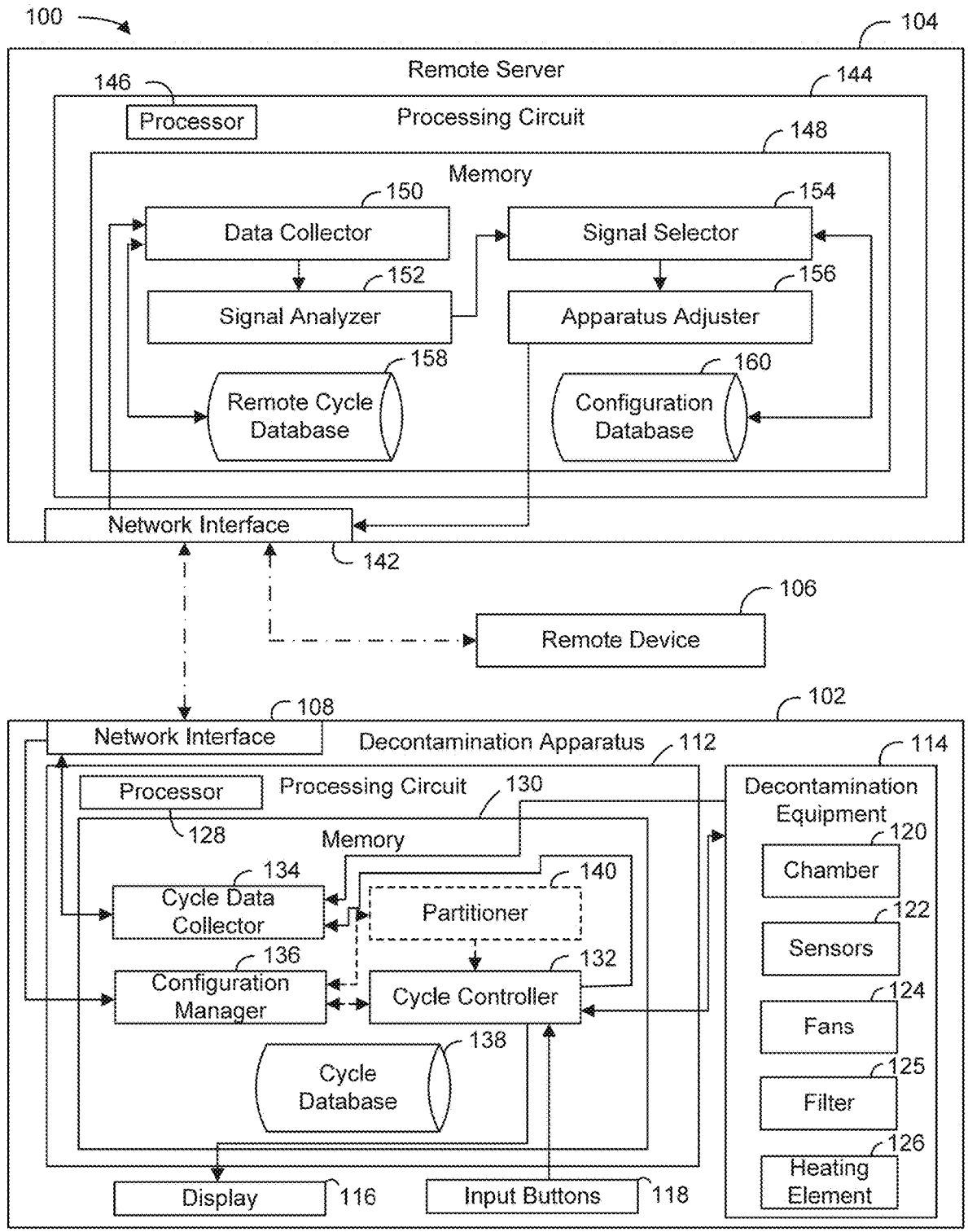
FIG. 1 is a block diagram of a system for remote control of decontamination of medical waste in a decontamination apparatus, in accordance with some embodiments of the present disclosure.

The foregoing and other features of the present disclosure will become apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings.

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the figures, can be arranged, substituted, combined, and designed in a wide variety of different configurations, all of which are explicitly contemplated and make part of this disclosure.

Attempted solutions for improving the decontamination process for medical equipment often require a pre-configured local apparatus to facilitate decontamination cycles as it is programmed. Such solutions are often static without a means for improving the decontamination process such as by improving the speed, energy efficiency, or consistency of successful decontamination cycles. Such solutions may also be unable to comply with changing regulatory requirements between different geographic regions or regulation changes within a geographic region. The solutions often involve a standalone device that does not adjust to changes in performance or issues that it is experiencing. These apparatuses may not have the capability to store decontamination cycle data, determine when or which errors occurred during a decontamination cycle, and/or be able to identify the source of such errors. Consequently, any degradation in the performance of the apparatus may not be identified until the apparatus becomes unusable and needs to be manually repaired. Further, without being able to determine the operation status of the apparatus, there may be instances in which an apparatus is not able to completely decontaminate medicate waste without a user realizing it, resulting in the user disposing of medical waste that could cause excess harm to the environment or for the apparatus to be out of compliance with the regulations of the region.

The systems and methods described herein provide for improvements to apparatuses that perform medical waste decontamination cycles. The systems and methods may enable a remote server to monitor such apparatuses as they perform medical waste decontamination cycles to make sure the devices are performing properly and are not experiencing excessive degradation in performance. The remote server may receive and store data for each medical waste decontamination cycle that the apparatus performs to identify the errors and differences in performance that the apparatus experiences over time. The remote server may communicate with the apparatus across a two-way wireless network interface (e.g., a cellular interface) without accessing a local network of a medical facility, ensuring data security and privacy protection for the medical facility, which often needs to comply with HIPAA rules and guidance and not let external devices have access to the facility's internal network. The remote server may identify various patterns that occur in the data and any degradation in performance of the apparatus. Upon noticing or identifying a particular pattern or degradation from the decontamination cycle data, such as a sustained increase in the length of time it takes for a chamber of the apparatus to heat up to a temperature capable of decontaminating medical waste, the remote server may identify a signal from its database that causes the apparatus to adjust and not experience such issues. In some instances, the remote server may be able to determine that the apparatus cannot be improved without a manual adjustment, and thus transmit a signal to the apparatus preventing it from performing another decontamination cycle. Consequently, the apparatus can avoid further degradation in performance and avoid a user unknowingly disposing of contaminated medical waste.

Referring now to FIG. 1, a block diagram of a system 100 for remote control of decontamination of medical waste in a decontamination apparatus is shown, in accordance with some embodiments of the present disclosure. System 100 is shown to include a decontamination apparatus 102, a remote server 104, and a remote device 106, in some embodiments. Decontamination apparatus 102 may be an apparatus that can facilitate and/or perform medical waste decontamination cycles so medical waste can be safely disposed of without excess harm to the environment. Remote server 104 may be a cloud server configured to store decontamination cycle data and perform analytics on the data using an operation policy to ensure decontamination apparatus 102 is operating correctly and effectively. Decontamination apparatus 102 may communicate with remote server 104 by transmitting signals via a network interface 108 of decontamination apparatus 102 to a network interface 110 of remote server 104. In turn, remote server 104 may communicate with decontamination apparatus 102 via network interface 110, thus creating a two-way communication channel.

Remote device 106 may comprise any type and form of media device or computing device, including a desktop computer, laptop computer, portable computer, tablet computer, wearable computer, embedded computer, smart television, set top box, console, Internet of Things (IoT) device or smart appliance, or any other type and form of computing device. Computing device(s) may be referred to variously as a client, device, client device, computing device, anonymized computing device or any other such term. Computing devices and intermediary modulator may receive media streams via any appropriate network, including local area networks (LANs), wide area networks (WANs) such as the Internet, satellite networks, cable networks, broadband networks, fiber optic networks, microwave networks, cellular networks, wireless networks, or any combination of these or other such networks. In many implementations, the networks may include a plurality of subnetworks which may be of the same or different types, and may include a plurality of additional devices (not illustrated), including gateways, modems, firewalls, routers, switches, etc.

A user may access a platform generated by remote server 104 via remote device 106 to view statistics and information about decontamination apparatus 102. In some embodiments, a user may upload new configurations to remote server 104 via remote device 106. For example, a user may provide inputs for new parameters for decontamination apparatus 102 to use when performing medical waste decontamination cycles. Remote server 104 may store such configurations in a database. Via the platform, a user, such as an entity who uses decontamination apparatus 102 to decontaminate waste, may view the data that was generated from each cycle that decontamination apparatus 102 performed. Furthermore, the platform enables remote server 104 to store related to the users or entities that use decontamination apparatus and the geographical location history of decontamination apparatus 102. A user may access the platform using login credentials specific to the user or to decontamination apparatus 102.

In brief overview, decontamination apparatus 102 may perform medical waste decontamination cycles on medical waste in a chamber of decontamination apparatus 102 and collect data about the medical waste decontamination cycles. Decontamination apparatus 102 may transmit data about the medical waste decontamination cycle to remote server 104 which can analyze the data according to an operation policy. Based on the analysis according to the operation policy, decontamination apparatus 102 may select a configuration signal including new parameters and/or new firmware and transmit the configuration signal to decontamination apparatus 102 to use when performing another decontamination cycle. By doing so, remote server 104 may adjust how decontamination apparatus 102 performs future medical waste decontamination cycles to perform medical waste decontamination cycles more efficiently and consistently (e.g., without errors).

Decontamination apparatus 102 may be an apparatus that facilitates the thermal processing of medical waste. As shown in FIG. 1, decontamination apparatus 102 may include network interface 108, a processing circuit 112, decontamination equipment 114, a display 116, and input buttons 118. Processing circuit 112 may communicate with equipment of decontamination equipment 114 to facilitate thermal processing of medical waste so the medical waste may be disposed of while minimizing the harm to the environment. For example, a user may insert medical waste into decontamination equipment 114. Processing circuit 112 may initiate and facilitate a decontamination cycle that melts the medical waste so it can be disposed of downstream in municipal landfills and/or down sewer systems without causing excessive harm to the environment (e.g., more harm than any other trash) and meet any regulatory compliance requirements for decontaminated medical waste.

Display 116 may include a display that is embedded in a housing of decontamination apparatus 102. Display 116 may display the current status of decontamination apparatus 102, the current state of a decontamination cycle (e.g., ramp-up, hold, or cool-down), time left for a decontamination cycle, a time left of a particular state of a decontamination cycle, etc. A user may interact with display 116 by selecting any of input buttons 118 to select options on display 116 or by pressing on display 116 itself in cases in which display 116 is a touchscreen. In some embodiments, display 116 may display the results of diagnostic tests that are run on decontamination apparatus 102. Display 116 may display any information related to decontamination apparatus 102 or a medical waste decontamination cycle that it facilitates or performs. Display 116 may update its user interface responsive to receiving signals from cycle controller 132 or any component of memory 130.

Medical waste can be grouped into multiple types of waste such as Sharps and Red Bag. Sharps can include blades and lancets, needles, carpules with visible blood or that are broken, extracted teeth, syringes, etc. Waste may be labeled as a Sharp because it contains sharp edges that could harm someone. Red Bag can include blood-saturated items, visibly contaminated protective equipment, blood and body fluids, blood-saturated gauze, blood-saturated bandages, etc. Red Bag waste may include any waste that could be infectious to the environment. Each of Sharp and Red Bag waste may include waste that is hazardous to the environment if it is not disposed of properly, consequently, each type of waste is subject to its own set of regulations that require it to be decontaminated before being disposed of through standard channels (e.g., a landfill or an incinerator). Each type of waste may be associated with different parameters for medical waste decontamination cycles such as different temperatures and lengths to ensure the waste is properly decontaminated and/or safe for disposal.

Network interface 108 may utilize various network protocols to facilitate communication with remote server 104. Network interface 108 may communicate with remote server 104 via a network protocol such as a cellular network protocol (e.g., 3G, 4G, 5G, LTE, etc.) or other network protocols such as Ethernet or Wi-Fi. Network interface 108 may communicate with remote server 104 over any network protocol. In some cases, although not shown, decontamination apparatus 102 may include the capability to communicate with remote server 104 over multiple network protocols (e.g., cellular and Ethernet). Consequently, if one network communication protocol is not available (e.g., there is poor cellular signal or there is not a nearby compatible Ethernet port), decontamination apparatus 102 may communicate with remote server 104 over another available network protocol. A network interface 110 of remote server 104 may transmit signals over the same network protocol back to decontamination apparatus 102, thus creating a two-way communication channel between decontamination apparatus 102 and remote server 104.

Advantageously, in embodiments in which network interface 108 of decontamination apparatus 102 utilizes a cellular network communication protocol, decontamination apparatus 102 may communicate with remote server 104 without accessing the local area network of a medical facility in which decontamination apparatus 102 is located. Such local area networks may have weak security or may be accessible to the public so people can access the internet while they are in the medical facility. Consequently, decontamination apparatus 102 may transmit data to remote server 104 without providing the data to a public network where a malicious party such as an eavesdropper can gain access to the data. Furthermore, because decontamination apparatus 102 may utilize a cellular network connection to connect to remote server 104, decontamination apparatus 102 may automatically be able to connect to remote server 104 upon being installed into a facility. Decontamination apparatus 102 may communicate with remote server 104 without having to be configured to access the local network of the facility for such communication, saving set-up time.

Decontamination equipment 114 is shown to include chamber 120, sensors 122, fans 124, filter 125, and a heating element 126. Each of components 120-126 may cooperate to decontaminate medical waste that is placed into chamber 120. Chamber 120 may be configured to receive and hold disposable containers such as Red Bags and Sharp containers. Chamber 120 may be formed of any rigid material that is capable of withstanding high temperatures such as temperatures between 300 and 500 degrees Fahrenheit (e.g., sterilization heat ranges) such as plastics, stainless steel, or other metals. Chamber 120 may be any shape such as cylindrical, spherical, cubic, rectangular, etc. Chamber 120 may be configured or made of any material to withstand any temperature.

Sensors 122 may be temperature sensors that are coupled or attached to chamber 120 and that are configured to detect the current temperature of or within chamber 120, such as during a medical waste decontamination cycle. Sensors 122 may include thermocouples, resistance temperature detectors, thermistors, or semiconductor-based integrated circuits that are configured to detect the temperature within chamber 120. Sensors 122 may include one, two, or any number of temperature sensors that are placed at different locations within chamber 120 or that are attached or fastened to an external face of chamber 120. Each sensor of sensors 122 may be configured to determine or generate data indicating the temperature of or within chamber 120 from its perspective and transmit data comprising the determined or generated data to processing circuit 112.

Fans 124 may be or include multiple fans positioned outside of chamber 120 but within a housing of decontamination apparatus 102 that helps facilitate temperature control of a medical waste decontamination cycle, such as to help cool down chamber 120. In some embodiments, fans 124 may be positioned on the back, bottom, and/or top of decontamination apparatus 102. The fan on the bottom may bring in air from the outside to blow cool air onto chamber 120 to cool down chamber 120. Additionally, the air may be directed within the housing of decontamination apparatus 102 to the circuitry of processing circuit 112 to keep the circuitry from overheating while chamber 120 is being heated. A fan on the back of decontamination apparatus 102 may allow the air that enters the housing of decontamination apparatus 102 to exit. The fan on the top may be used to allow fumes that are generated during a medical waste decontamination cycle to exit chamber 120 and/or the housing of decontamination apparatus 102.

In some embodiments, before the fumes generated during the medical waste cycles exit decontamination apparatus 102, the fumes may pass through filter 125. Filter 125 may be connected to an area underneath chamber 120 in a housing of decontamination apparatus 102 via a tube, channel, or any other connection device or channeling mechanism. Filter 125 may be an antibiological material filter that can filter viral and bacterial material. In some embodiments, filter 125 may be or include a charcoal material. Advantageously, a dual stage, anti-viral/anti-bacterial-charcoal filter may have the ability to capture viruses or bacteria from the fumes generated from heated medical waste. Filter 125 may capture viruses and bacteria generated from the heated waste as chamber 120 is heated.

Heating element 126 may be any heating element that is coupled or attached to chamber 120 and that is configured to heat up chamber 120 during a medical waste decontamination cycle. Heating element 126 may be or include a heating band (e.g., an electric heating band), an electric coil (e.g., a flat coil heater, a maxi coil heater, an axial clamp heater, a formable coil heater, a round coil heater, etc.), an induction heater, etc. Heating element 126 may include one or more of such heating elements that are coupled and controlled by processing circuit 112 to heat chamber 120 during a medical waste decontamination cycle. Heating element 126 may be heated to different temperatures depending on the signal it receives from processing circuit 112.

Processing circuit 112 is shown to include a processor 128 and memory 130, in some embodiments. Processing circuit 112 may be implemented as a general-purpose processor, an application specific integrated circuit ("ASIC"), one or more field programmable gate arrays ("FPGAs"), a digital-signal-processor ("DSP"), circuits containing one or more processing components, circuitry for supporting a microprocessor, a group of processing components, or other suitable electronic processing components. Processor 128 may include an ASIC, one or more FPGAs, a DSP, circuits containing one or more processing components, circuitry for supporting a microprocessor, a group of processing components, or other suitable electronic processing components. In some embodiments, processor 128 may execute computer code stored in memory 130 to facilitate the activities described herein. Memory 130 may be any volatile or non-volatile computer-readable storage medium capable of storing data or computer code relating to the activities. According to an exemplary embodiment, memory 130 may include computer code modules (e.g., executable code, object code, source code, script code, machine code, etc.) for execution by processor 128.

Input buttons 118 may include one or more buttons that a user may use to initiate medical waste decontamination cycles. In some embodiments, input buttons 118 may include a start/stop button, a sharps button, a red bag waste button, etc. Input buttons 118 may include any number of buttons. Upon inserting medical waste into chamber 120, a user may select one of the Sharp or Red Bag Waste buttons to indicate the type of waste that was placed into chamber 120. Selection of the Sharp or Red Bag Waste buttons may cause decontamination apparatus 102 to perform a medical waste decontamination cycle with parameters that correspond to the selected button. The user may then select the start/stop button to indicate to start or stop a medical waste decontamination cycle to decontaminate the inserted waste. Upon selection of any of input buttons 118, the selected input button may transmit a signal to processing circuit 112 indicating which input button was selected, thereby initiating a medical waste decontamination cycle.

Memory 130 is shown to include a cycle controller 132, a cycle data collector 134, a configuration manager 136, and a cycle database 138, in some embodiments. In some embodiments, memory 130 may also include a partitioner 140. In brief overview, components 132-140 may cooperate to facilitate medical waste decontamination cycles via decontamination equipment 114, collect data generated during such medical waste decontamination cycles, and transmit the collected data to remote server 104. Components 132-138 may receive signals, in some cases comprising new configuration data generated by remote server 104 based on the collected data, from remote server 104 and facilitate medical waste decontamination cycles based on the received signals.

Cycle controller 132 may comprise programmable instructions that, upon execution, cause processor 128 to facilitate medical waste decontamination cycles. A medical waste decontamination cycle may be or include a series of steps that the components of decontamination apparatus 102 perform to decontaminate waste that is placed into chamber 120. A medical waste decontamination cycle may include thermally decontaminating medical waste in chamber 120. As described herein, a medical waste decontamination cycle may be a decontamination cycle, a cycle, or a medical decontamination cycle. Cycle controller 132 may facilitate a medical waste decontamination cycle by heating medical waste in chamber 120 for a predetermined length of time and then letting the medical waste cool until sensors 122 detect or generate data that indicates that the waste inside chamber 120 can be handled (e.g., the waste or chamber 120 has reached a temperature below a predetermined threshold set by an administrator or user). During the medical waste decontamination cycle, cycle controller 132 may control the latches of a lid of decontamination apparatus 102 that covers chamber 120 to be locked shut so the lid cannot be opened or jarred open during the medical waste decontamination cycle. The lid may include two or any number of latches to help secure the lid in place. Upon sensors 122 generating data indicating that chamber 120 has reached below a temperature threshold, cycle controller 132 may unlock the latches so the lid may be opened and a user may remove the decontaminated medical waste from chamber 120. Such a decontamination cycle may be initiated by a user upon selection of one of input buttons 118 or at a specific time as programmed remotely by remote server 104.

In some embodiments, a medical waste decontamination cycle may include a plurality of states. For example, a medical waste decontamination cycle may include a ramp-up period in which chamber 120 heats up, a hold period in which chamber 120 remains at a substantially constant temperature, and a cool-down period in which the temperature of chamber 120 cools down. Each of the states may be configured by an administrator.

During the ramp-up period, cycle controller 132 may cause chamber 120 to heat up from a starting point (e.g., room temperature) to a predetermined setpoint (e.g., a set temperature). The ramp-up period may be a predetermined period of time in which the temperature of chamber 120 heats up to the predetermined setpoint. Upon receiving an input from a user, cycle controller 132 may initiate the ramp-up period by locking the lid of decontamination apparatus 102. The lid may remain locked until decontamination apparatus 102 completes a medical waste decontamination cycle. Cycle controller 132 may cause (e.g., transmit signals to) heating element 126 to heat chamber 120 until heat chamber 120 reaches the predetermined setpoint temperature. The predetermined setpoint temperature may be 300 degrees Fahrenheit, 350 degrees Fahrenheit, 380 degrees Fahrenheit, 400 degrees Fahrenheit, or any other temperature.

In some embodiments, to heat up chamber 120, cycle controller 132 plots a straight-line temperature curve between the starting point and the predetermined setpoint. Cycle controller 132 may heat chamber 120 according to the straight-line temperature curve, thereby heating chamber 120 in a controlled fashion. The straight-line temperature curve may include expected temperature points of chamber 120 at different points in time of the ramp-up period. As cycle controller 132 causes heating chamber 120 to heat up during the ramp-up period, cycle controller 132 may continuously determine the current temperature of chamber 120. In some cases, to do so, cycle controller 132 may periodically read the temperature of the thermistors or other temperature sensors of sensors 122. Cycle controller 132 may do so at any interval such as 10 times a second. Cycle controller 132 may determine the average of the temperature reading between the temperature sensors to determine the current temperature and compare the current temperature to the expected temperature at the current time of the ramp-up period. Responsive to determining the current temperature is lower than the expected temperature, cycle controller 132 may transmit signals to heating element 126 to turn or keep heating element 126 on (or increase its temperature). However, responsive to determining the current temperature is equal to or greater than the expected temperature, cycle controller 132 can transmit signals to heating element 126 to turn heating element 126 off (or decrease its temperature). Cycle controller 132 may continue this process until cycle controller 132 receives data indicating that chamber 120 has reached the predetermined setpoint. Responsive to determining chamber 120 has reached the predetermined setpoint, cycle controller 132 may cause the decontamination cycle to enter the hold period of the cycle.

In some embodiments, cycle controller 132 may identify errors that occurred during the ramp-up period. To do so, cycle controller 132 may compare the determined current temperature to a threshold. Cycle controller 132 may determine a difference between the current temperature and the expected temperature of the straight-line temperature curve. Cycle controller 132 may compare the determined difference to a threshold (e.g., 20 degrees Fahrenheit). The threshold may be any temperature. Responsive to determining the determined difference exceeds the threshold, cycle controller 132 may determine an error occurred. However, responsive to determining the determined difference does not exceed the threshold, cycle controller 132 may determine the ramp-up period is operating in a normal state (e.g., without an error).

In some cases, cycle controller 132 may only determine or identify an error after determining the temperature difference is above the threshold for a predetermined amount of time (e.g., 90 seconds). Cycle controller 132 may determine that the temperature difference between the expected temperature and the actual temperature within chamber 120 exceeds the threshold at each instance (or in some cases a number of instances, such as 95%, exceeding a threshold within a moving window time period of the predetermined amount of time) for 90 seconds and identify an error accordingly.

In some embodiments, cycle controller 132 may identify an error in data collection during a decontamination cycle. For example, cycle controller 132 may receive temperature readings from multiple temperature sensors of sensors 122 and compare the temperature readings with each other. Cycle controller 132 may determine the differences between the temperature readings. Responsive to determining a difference in temperature readings exceeds a threshold, cycle controller 132 may identify an error occurred during the ramp-up period of the decontamination cycle. In some embodiments, responsive to determining an error has occurred or will occur, cycle controller 132 may restart the decontamination cycle. Cycle controller 132 may perform medical waste decontamination cycles until cycle controller 132 facilitates a decontamination cycle without identifying or determining an error occurred. Accordingly, cycle controller 132 can ensure that the waste in chamber 120 has been properly decontaminated (e.g., that a complete medical waste decontamination cycle has been performed) before unlocking the latches for a user to open the lid and remove the medical waste from chamber 120.

Cycle controller 132 may facilitate the hold period of the decontamination cycle according to parameters and values for parameters in a parameter file. A hold temperature (e.g., the predetermined setpoint temperature) and a length of the hold period may be values stored in the parameter file. The values may be manually entered by a user or an administrator or automatically generated as described herein. The length may be 90 minutes, 120 minutes, 150 minutes, or any other length. As with the ramp-up period, cycle controller 132 may monitor the temperature of chamber 120 to maintain its temperature at the predetermined setpoint. Cycle controller 132 may identify errors similar to the ramp-up period by identifying instances in which the temperature of chamber 120 exceeds or is lower than the hold temperature by a threshold and/or when the temperature sensors are providing temperature readings with values having differences that exceed a threshold. In each of these instances, cycle controller 132 may identify that an error occurred during the hold period. Cycle controller 132 may maintain the hold period until the length of the hold period has been reached. Upon reaching the end of the length of the hold period, cycle controller 132 may initiate the cool-down period.

The cool-down period may be a period of time in which cycle controller 132 turns off heating element 126, causing the temperature of chamber 120 to cool down. The cool-down period may not have a predetermined length, but rather last until the temperature of chamber 120 reaches a lower bound or threshold. For example, the cool-down period may last until cycle controller 132 receives data indicating that chamber 120 is 105 degrees Fahrenheit or lower. The lower bound or temperature may be any temperature. Cycle controller 132 may periodically determine the temperature of chamber 120 similar to the ramp-up period and the hold period and continuously compare the determined temperature to the lower bound or threshold. Responsive to determining chamber 120 has reached or is below the lower bound or threshold, cycle controller 132 may end the medical waste decontamination cycle and unlock the latches that were previously keeping the lid in place. Upon completion of the cycle, the waste may be decontaminated for disposal in a landfill.

During the cool-down period, cycle controller 132 may control the spin rates of fans 124 to facilitate cooling. To do so, cycle controller 132 may cause the fan on the bottom of decontamination apparatus 102 to spin faster to cause cool air to hit the bottom of chamber 120 while the fans on the top and/or the side to spin slower to facilitate the air leaving decontamination apparatus 102. Cycle controller 132 may cause the fans to spin in any pattern to facilitate cooling.

Cycle controller 132 may operate decontamination apparatus 102 according to a set of parameters. The parameters may include, but are not limited to, a testing protocol, fan speeds, ramp-up times and temperatures, cycle times and temperatures, thermistor or temperature sensor usage, diagnostic displays, etc. The parameters may be stored on an SD-card of decontamination apparatus 102 or otherwise in memory 130 and may be loaded upon startup. The parameters may be stored in a parameter file as described above. The parameters may be set or updated while cycle controller 132 is operating a medical waste decontamination cycle or decontamination apparatus 102 is idle but turned on. In some embodiments, the parameters may be stored in memory 130 of decontamination apparatus 102 to be implemented upon the next re-boot of decontamination apparatus 102.

In some embodiments, cycle controller 132 may retrieve parameters from the parameter file of the SD-card and store the parameters in memory 130 upon boot-up of decontamination apparatus 102. Upon initiating a medical waste decontamination cycle, cycle controller 132 may retrieve the parameters from memory 130 as it facilitates the cycle. For example, as cycle controller 132 facilitates the ramp-up period of the cycle, cycle controller 132 may retrieve the parameters associated with the hold period (e.g., the hold period temperature or the hold period length) of the cycle to initiate the hold period responsive to completion of the ramp-up period. Configuration manager 136 may also store the new configuration on the SD card so the new configuration may be retrieved upon boot up for future medical waste decontamination cycles.

An advantage of retrieving parameters for medical waste decontamination cycles from memory 130 as it performs a cycle is, by doing so, remote server 104 may update the configuration of decontamination apparatus 102 while decontamination apparatus 102 performs a medical waste decontamination cycle. For example, remote server 104 may transmit a signal for a new configuration for decontamination apparatus 102 such as a change in fan speed, a change in hold temperature, or a change in cycle length to decontamination apparatus 102 while cycle controller 132 performs a medical waste decontamination cycle. Configuration manager 136 may store the updated configuration in memory 130 upon receiving the new parameters. Cycle controller 132 may retrieve the new parameters as it performs the medical waste decontamination cycle and perform the medical waste decontamination cycle with the updated parameters. For example, if the new configuration comprises new fan speeds, cycle controller 132 may update the fan speeds of the medical waste decontamination cycle with the new fan speeds. If the new configuration comprises a new hold temperature, cycle controller 132 may cause heating element 126 to heat chamber 120 to the new hold temperature. Cycle controller 132 may update any parameters during a medical waste decontamination cycle.

Changing the parameters of a medical waste decontamination cycle may be advantageous when remote server 104 determines decontamination apparatus 102 is not performing a decontamination cycle properly (e.g., the cycle is not compliance with local regulations or the cycle is not adequately decontaminating the medical waste within chamber 120). Decontamination apparatus 102 may receive new configurations to resolve such issues and update how decontamination apparatus performs the current cycle mid-cycle to successfully decontaminate the medical waste within chamber 120.

Cycle controller 132 may also be configured to implement a testing protocol upon a series of button presses of input buttons 118. The testing protocol can include self-tests for several internal elements such as to test display 116, the backlight of display 116, input buttons 118 (e.g., for normal and long presses), the operation of fans 124, the operation of heating element 126, the operability of sensors 122, lid latch functionality and control, network connectivity, etc. Cycle controller 132 may send signals to the relevant components or simulate signals from the components to test whether the functionality of each component is operating properly. Cycle controller 132 may generate results from the test and write them to a file. A user may access the file through a USB port of decontamination apparatus 102 to determine whether decontamination apparatus 102 is functioning properly.

Cycle data collector 134 may comprise instructions that, upon execution, cause processor 128 to collect data about decontamination apparatus 102. While cycle controller 132 facilitates medical waste decontamination cycles, cycle data collector 134 may collect data that sensors 122 and cycle controller 132 generate during the respective medical waste decontamination cycles. For example, cycle data collector 134 may collect temperature readings and/or corresponding timestamps from sensors 122 and error identifications from cycle controller 132. In some embodiments, cycle data collector 134 may receive temperature readings, timestamps, and error identifications from cycle controller 132.

Cycle data collector 134 may collect such data and transmit the data to remote server 104 via network interface 108 for processing.

In some embodiments, in addition to or instead of temperature and/or error data, cycle data collector 134 collects and transmits data related to decontamination apparatus 102 as it was configured during the respective medical waste decontamination cycle, other data about the respective decontamination cycle, and/or network configuration data of decontamination apparatus 102. For example, in a data packet following completion of a medical waste decontamination cycle, cycle data collector 134 may send an identification of the firmware operating on processing circuit 112 during the medical waste decontamination cycle, the international mobile equipment identity (IMEI) of decontamination apparatus 102, cell network strength, the IP address of decontamination apparatus 102, the minimum and maximum temperature achieved during the medical waste decontamination cycle, the length of the medical waste decontamination cycle, the number of times the medical waste decontamination cycle restarted, the time the medical waste decontamination cycle started, the time the medical waste decontamination cycle ended, the type of the decontamination cycle (e.g., the type of waste that decontamination apparatus 102), etc. Cycle data collector 134 may send the data in a byte array. Cycle data collector 134 may send any data associated with decontamination apparatus 102, the network connection of decontamination apparatus 102, and/or the medical waste decontamination cycle to remote server 104.

Cycle data collector 134 may generate and transmit data to remote server 104 by encapsulating the data of decontamination apparatus 102 and/or a decontamination cycle into a data packet. Cycle data collector 134 may transmit encapsulated data packets to remote server 104 via an MQTT protocol over the TCP/IP layer of the network stack of decontamination apparatus 102. For example, cycle data collector 134 may be an application run by processor 128 of decontamination apparatus 102 that communicates with a corresponding application on remote server 104 via the MQTT protocol over network interface 108. The application may include each or a portion of cycle controller 132, cycle data collector 134, configuration manager 136, and/or partitioner 140. Cycle data collector 134 may receive or collect data about decontamination apparatus 102 that is generated or associated with a decontamination cycle that cycle controller 132 facilitates. Cycle data collector 134 may generate a data packet including the data and transmit the data packet to remote server 104 via the MQTT protocol. Cycle data collector 134 may use any network protocol to transmit the data to remote server 104.

In some embodiments, in addition to or instead of transmitting the data of a medical waste decontamination cycle and/or information about decontamination apparatus 102 to remote server 104, cycle data collector 134 (or any other component of decontamination apparatus 102) may store the data in cycle database 138. Cycle database 138 may be a dynamic database that includes medical waste decontamination cycle data. Cycle database 138 can be a graph database, MySQL, Oracle, Microsoft SQL, PostgreSql, DB2, document store, search engine, key-value store, etc. Cycle database 138 may be configured to hold any amount of data and can be made up of any number of components. Cycle data stored in the cycle database 138 may comprise data that is associated with individual medical waste decontamination cycles and/or information about decontamination apparatus 102 while decontamination apparatus 102 performs such cycles.

In some embodiments, to transmit data to remote server 104, cycle data collector 134 may implement a positive acknowledgment process. The positive acknowledgment process may include steps that cycle data collector 134 may take to ensure the data for medical waste decontamination cycles are successfully transmitted and stored at remote server 104. The positive acknowledgment process may begin once a medical waste decontamination cycle is completed and cycle data collector 134 has collected the data associated with the medical waste decontamination cycle. Cycle data collector 134 may store the data about the decontamination cycle in cycle database 138 or an allocated portion of memory 130. Additionally, cycle data collector 134 may encapsulate the data and transmit the data to remote server 104 via network interface 108 using, for example, the MQTT protocol. Via an application, remote server 104 may receive the data packet and send an acknowledgment packet back to remote server 104 indicating that the message has been accepted. Cycle data collector 134 may receive the acknowledgment packet and continue to send the data packet in messages to remote server 104 at a $2^x$ decreasing frequency (e.g., one second, two seconds, four seconds, eight seconds, 16 seconds, . . . one hour, etc.). In some embodiments, cycle data collector 134 may send messages at a decreasing frequency until cycle data collector 134 sends the messages every hour (or another time interval), in which case cycle data collector 134 may continuously send the messages every hour at a constant interval. Cycle data collector 134 may transmit the messages at any frequency and at any descending or ascending rate. While cycle data collector 134 sends the data to remote server 104, remote server 104 may load the data into a database and run a series of processes to check the data for errors (e.g., for errors that occurred during transmission of the data). Responsive to completing the processes, remote server 104 may send a message back to decontamination apparatus 102 indicating for decontamination apparatus 102 to stop sending data packets for the decontamination cycle. Cycle data collector 134 may receive the message and stop sending messages including data packets associated with the decontamination cycle and remove or delete data associated with the decontamination cycle from cycle database 138 or the data's allocated portion of memory 130. Consequently, cycle data collector 134 can ensure that the data for a decontamination cycle is not lost while avoiding storing the data in memory 130 of decontamination apparatus 102, which may be limited due to the compact size of decontamination apparatus 102 or to the security risk of malicious parties such as hackers that have access to the facility in which decontamination apparatus 102 is located. A copy of each message that is exchanged between decontamination apparatus 102 and remote server 104 may be stored in a database of remote server 104.

In some instances, decontamination apparatus 102 may not be able to connect with remote server 104. For example, decontamination apparatus 102 may not have a good network connection or remote server 104 may be experiencing networking issues. In such instances, cycle data collector 134 may continuously transmit (at intervals of decreasing frequency as described above) data packets for any number of decontamination cycles until cycle data collector 134 receives a signal indicating data for the respective cycle has been successfully received and/or processed. Cycle data collector 134 may delete or remove the data associated with the decontamination cycle from memory 130 upon receiving the signal from remote server 104.

In some embodiments, decontamination apparatus 102 may transmit signals to remote server 104 upon boot-up. The signals may include data about decontamination apparatus 102 such as its current firmware, IMEI, network connectivity, IP address, etc. Remote server 104 may analyze these signals as described herein to determine whether to send a signal with a new configuration back to decontamination apparatus 102.

Remote server 104 may be one or more servers that is configured to store data it receives from decontamination apparatus 102 and transmit new configurations to decontamination apparatus 102 via a network interface (e.g., network interface 110). Remote server 104 may be or include one or more cloud servers. In some instances, remote server 104 may be a dedicated server to decontamination apparatus 102 and/or multiple apparatuses that are similar to decontamination apparatus 102. In still further instances, remote server 104 may be or include a server that is dedicated to storing data generated from the facility, such as a hospital, in which decontamination apparatus 102 is operating. Remote server 104 is shown to include network interface 110 and processing circuit 144, in some embodiments. Processing circuit 144 is shown to include a processor 146 and memory 148, in some embodiments. Processor 146 and memory 148 may be similar to processor 128 and memory 130 of decontamination apparatus 102, respectively.

Memory 148 is shown to include a data collector 150, a signal analyzer 152, a signal selector 154, an apparatus adjuster 156, a remote cycle database 158, and a configuration database 160, in some embodiments. In brief overview, remote server 104 may receive data packets comprising operation data of decontamination apparatus 102 that decontamination apparatus 102 collects as it performs medical waste decontamination cycles. The operation data may include data generated for the medical waste decontamination cycle, configuration data of decontamination apparatus 102 during the cycle, and network data about decontamination apparatus 102. Remote server may 104 analyze the operation data according to an operation policy. Responsive to determining there is a new configuration for decontamination apparatus 102, remote server 104 may select a signal corresponding to the new configuration and transmit the signal to decontamination apparatus 102 via network interface 110, causing decontamination apparatus 102 to operate under the new configuration.

In some embodiments, the new configurations may be tagged as temporary or permanent changes to the configuration of decontamination apparatus 102. Temporary new configurations may have or include a setting that indicates a length of time to implement the configuration. Decontamination apparatus 102 may identify the tags from the signals it receives from remote server 104 and only implement the configuration during the length of time before reverting back to the previous configuration. Such may be advantageous if the new configuration is meant to lower the stress placed on decontamination apparatus 102 components for a period of time but causes other deficiencies such as an increase in cool-down time. By including the setting with the temporary tag, remote server 104 may enable decontamination apparatus 102 to recover while still performing medical waste decontamination cycles.

Data collector 150 may include programmed instructions that, when executed by processor 146, cause processor 146 to collect data that remote server 104 receives from decontamination apparatus 102 via network interface 110. Data collector 150 may be or be a part of an application that communicates with the application of decontamination apparatus 102 via the MQTT protocol. Data collector 150 may receive the data packets that correspond to a medical waste decontamination cycle from decontamination apparatus 102 and extract the data from the data packets. Upon extracting the data, data collector 150 may store the data in remote cycle database 158. Upon receiving the data packet from decontamination apparatus 102, data collector 150 may transmit a message back to decontamination apparatus 102 indicating that data collector 150 has received the data. In some embodiments, data collector 150 may additionally check the data for errors that occurred during transmission and send a signal back to decontamination apparatus 102 once it determines that there were no transmission errors. Data collector 150 may additionally or instead transmit the data to signal analyzer 152 for further processing.

Remote cycle database 158 may be a database similar to cycle database 138 of decontamination apparatus 102. Remote cycle database 158 may store data related to decontamination cycles that decontamination apparatus 102 performs. Data from the decontamination cycles that is stored in remote cycle database 158 may be associated with a respective instance (e.g., a tag) of the medical waste decontamination cycle. Memory 148 may be larger than memory 130 of decontamination apparatus 102. Consequently memory 148 may be able to store data for large amounts of medical waste decontamination cycles to maintain a record of the data that is generated by decontamination apparatus 102. While data that corresponds to medical waste decontamination cycles is periodically deleted from cycle database 138, remote cycle database 158 may maintain records of medical waste decontamination cycles over time. Components (e.g., signal analyzer 152) of remote server 104 may retrieve data from remote cycle database 158 to determine how decontamination apparatus 102 is performing over time and any degradations in performance, something decontamination apparatus 102 may not be able to do given its limited memory capacity.

Signal analyzer 152 may be or include programmed instructions that, upon being executed by processor 146, cause processor 146 to analyze signals corresponding to decontamination cycles according to an operation policy. The operation policy may comprise a series of rules and/or thresholds to which signal analyzer 152 may compare the data of one or more decontamination cycles to determine whether remote server 104 should transmit new configuration data to decontamination apparatus 102. In some embodiments, signal analyzer 152 may analyze signals according to the operation policy by comparing the data of the signals to configuration database 160.

Similar to cycle database 138 and remote cycle database 158, configuration database 160 may be a dynamic database that includes configurations for decontamination apparatus 102. Cycle database 138 can be a graph database, MySQL, Oracle, Microsoft SQL, PostgreSql, DB2, document store, search engine, key-value store, etc. Cycle database 138 may be configured to hold any amount of data and can be made up of any number of components. A user may add new configurations to configuration database 160 via a user device (e.g., remote device 106) over time. The configurations may be associated with or linked to geographic locations, pattern-decontamination cycle configuration pairs, configurations for decontamination equipment 114 such as sensors 122, fans 124, and/or heating element 126, configurations related to how cycle controller 132 generates data when facilitating a medical waste decontamination cycle, etc. In some embodiments, the configurations in configuration database 160 may include new parameters for decontamination apparatus 102 and similar devices to use to perform medical waste decontamination cycles. In some embodiments, the configurations in configuration database 160 include firmware updates for decontamination apparatus 102 and similar devices.

In one example, signal analyzer 152 may determine whether to transmit new firmware to decontamination apparatus 102. Signal analyzer 152 may extract data identifying the current configuration of the firmware of decontamination apparatus 102 from a data packet and compare the firmware to the most recently uploaded firmware stored in configuration database 160. Responsive to determining there is a more recent version of firmware, signal analyzer 152 may transmit a signal to signal selector 154 indicating to select the most recent firmware to transmit to decontamination apparatus 102. In some embodiments, the new firmware may be tagged with units, such as decontamination apparatus 102 for which it cannot be downloaded, which can be advantageous if the new firmware is not compatible with the new firmware. Before transmitting the new firmware to decontamination apparatus 102, signal analyzer 152 may determine decontamination apparatus 102 may receive the new firmware, or that it is otherwise compatible to operate with the new firmware.

In another example, signal analyzer 152 may extract the error data from the data packet of a decontamination cycle and compare the error data to a set of pattern-decontamination cycle configuration pairs that are stored in configuration database 160. Each pattern-decontamination cycle configuration pair may be associated with one or more errors that can occur during a decontamination cycle (or multiple decontamination cycles). If the errors of a data packet correspond to such a pattern-decontamination cycle configuration pair, signal analyzer 152 may transmit a signal to signal selector 154 indicating to select a configuration for decontamination apparatus 102 that corresponds to resolving the errors associated with a pattern-decontamination cycle configuration pair. Consequently, remote server 104 may automatically determine a new configuration for decontamination apparatus 102 to resolve issues that are causing decontamination apparatus 102 to run multiple medical waste decontamination cycles to decontaminate one set of medical waste (e.g., as a result of starting a cycle over multiple times after experiencing one or more errors) and/or to not properly decontaminate medical waste during such a cycle. By transmitting the new configuration data to resolve these errors, remote server 104 may cause decontamination apparatus 102 to use less energy (e.g., because multiple cycles are not needed to decontaminate one set of medical waste) and to more effectively and consistently perform decontamination cycles without such errors occurring.

In some embodiments, a pattern-decontamination cycle configuration pair may correspond to a change in how cycle controller 132 of decontamination apparatus 102 operates during a medical waste decontamination cycle. For example, cycle controller 132 may facilitate a medical waste decontamination cycle in one configuration in which cycle controller 132 determines the temperature of chamber 120 by taking the average temperature of the thermistors or sensors 122. Cycle controller 132 may detect errors related to the temperatures that sensors 122 detect and/or for which sensors 122 generate data. Signal analyzer 152 may analyze this error data from a data packet corresponding to a medical waste decontamination cycle and identify a pattern-decontamination cycle configuration pair with a new configuration in which cycle controller 132 determines the temperature of chamber 120 based on the temperature from only one of sensors 122. For example, in the new configuration, cycle controller 132 may determine the temperature of chamber 120 to be the highest or lower temperature that is generated for a point in time by sensors 122. A new configuration may include any configuration for facilitating a configuration cycle.

In another example, a pattern-decontamination cycle configuration pair may correspond to a change in how cycle controller 132 controls the temperature of chamber 120 during a medical waste decontamination cycle. For example, signal analyzer 152 may identify errors in which chamber 120 is not heating up or cooling down as quickly as is intended. Cycle controller 132 may determine errors during a cycle in which chamber 120 is outside of the expected temperature. Signal analyzer 152 may identify these errors from a data packet that corresponds to the respective medical waste decontamination cycle and compare them to configuration database 160. Signal analyzer 152 may identify a pattern-decontamination cycle configuration pair that corresponds to the error and the configuration of the pattern-decontamination cycle configuration pair. The configuration may include or be a new configuration for heating element 126 and/or a fan (e.g., the bottom fan) of fans 124. The new configuration for heating element 126 may be an increase (or decrease) in the electricity that heats up one or more of the heating elements of heating element 126 or a corresponding higher temperature. The new configuration for the fan may be an increase (or decrease) in its revolution speed that causes more air to go through the bottom of decontamination apparatus 102. The new configurations for heating element 126 or the fan may be any configuration. Consequently, by using the pattern-decontamination cycle configuration pairs, signal analyzer 152 can identify new configurations that can cause decontamination apparatus 102 to operate and experience fewer errors while facilitating medical waste decontamination cycles.

In yet another example, signal analyzer 152 may remotely ensure that decontamination apparatus 102 is operating in compliance with local geographical regulations for decontamination of medical waste while still decontaminating such waste. Signal analyzer 152 may receive geographical location data and determine the geographical location of decontamination apparatus 102. Signal analyzer 152 may receive the geographical location as an input from a user device (e.g., remote device) or in the data that decontamination apparatus 102 transmits to remote server 104. For example, signal analyzer 152 may extract the IP address of decontamination apparatus 102 from a data packet that decontamination apparatus 102 transmits to remote server 104 that corresponds to the medical waste decontamination cycle. Signal analyzer 152 may determine a general location of decontamination apparatus 102 from the IP address (e.g., by comparing the IP address to a table identifying relationships between IP addresses and geographical locations). Signal analyzer 152 may compare the location to configuration database 160, which may store associations between cycle lengths of medical waste decontamination cycles and such locations. Signal analyzer 152 may identify the cycle length that corresponds to the general location of the IP address from configuration database 160. Signal analyzer 152 may compare the identified cycle length to a cycle length that signal analyzer 152 extracts from the data packet. Responsive to identifying a difference in cycle lengths, signal analyzer 152 may transmit a signal to signal selector 154 indicating to select a signal with a cycle length that corresponds to the location of the IP address. Otherwise, responsive to the cycle length of the location of the IP address matching the corresponding cycle length in configuration database 160, signal analyzer 152 may not transmit a signal to signal selector 154.

In some embodiments, the cycle length that signal analyzer 152 identifies from configuration database 160 corresponds to a length of the hold period of a configuration cycle. While the ramp-up period length and the cool-down period length regulations may be similar across different geographical regions, different regions may require medical waste decontamination cycles to have different hold period lengths. Similarly, in some embodiments, instead of or in addition to having different hold-period lengths, regulations of different geographic regions may require decontamination apparatus 102 to have different hold period temperatures. Signal analyzer 152 may similarly identify the hold temperature of the region. By implementing the systems and methods described herein, signal analyzer 152 may determine different hold period lengths and/or temperatures based on the IP address of decontamination apparatus 102. Because the IP address can change as decontamination apparatus 102 changes geographic locations (and therefore accesses the network via a new connection), signal analyzer 152 may automatically determine regulation-compliant cycle lengths and temperatures for decontamination apparatus 102 based on the IP address included in the data packet of the most recent decontamination cycle. Signal analyzer 152 may transmit a signal to signal selector 154 indicating the signal or new configuration for signal selector 154 to select from configuration database 160 that includes the cycle length and/or hold temperature that corresponds to the location of decontamination apparatus 102. Receipt of the signal may cause signal selector 154 to select a signal with the configuration data for compliant cycle lengths and temperatures for transmission to decontamination apparatus 102. Furthermore, for each cycle that is performed, signal analyzer 152 may identify and store a geographical location for the cycle.

In yet another example, signal analyzer 152 may maintain and increment a counter indicating the number of medical waste decontamination cycles decontamination apparatus 102 has performed. For each medical waste decontamination cycle for which signal analyzer 152 receives data, signal analyzer 152 may increment a count of the counter, thereby maintaining a count of the number of medical waste decontamination cycles that decontamination apparatus has performed. After incrementing the count of the counter, for each indication, signal analyzer 152 may compare the incremented count to a threshold. The threshold may be a predetermined threshold set by a user that represents the number of medical waste decontamination cycles decontamination apparatus 102 may perform before degrading to where it cannot effectively decontaminate waste. An example of such degradation may be a degradation in filter 125, which may not operate effectively after a number of cycles and may need to be replaced. Signal analyzer 152 may continue incrementing the counter for decontamination apparatus 102 until signal analyzer 152 determines the count exceeds or otherwise satisfies the threshold. Upon satisfying the threshold, signal analyzer 152 may cause apparatus adjuster 156 to transmit a signal to apparatus adjuster 156, thus causing apparatus adjuster 156 to transmit an alert to remote device 106 indicating that decontamination apparatus 102 has performed a number of medical waste decontamination cycles that exceed the threshold. Remote device 106 may receive the alert and send a message to an administrator or other user of decontamination apparatus 102 to stop using decontamination apparatus 102.

In some embodiments, in addition to sending alerts to remote device 106, apparatus adjuster 156 may generate and transmit a user interface indicating the data that remote server 104 has collected about decontamination apparatus 102 from the operation data it has received. A user may view and access the data from a display of remote device 106.

In some embodiments, instead of causing apparatus adjuster 156 to send an alert to remote device 106, signal analyzer 152 may send a signal to signal selector 154 indicating for signal selector 154 to select a signal from configuration database 160 that prevents decontamination apparatus 102 from performing another medical waste decontamination cycle until it is reviewed and/or serviced to make sure it can still adequately decontaminate waste in compliance with local regulations. Consequently, remote server 104 may ensure that decontamination apparatus 102 is capable of effectively decontaminating medical waste for each medical waste decontamination cycle that it performs.

In some embodiments, signal analyzer 152 may maintain a count for the counter for medical waste decontamination cycles for specific time periods and reset the counter after each time period. To do so, signal analyzer 152 may increment the count of the counter for each medical waste decontamination cycle that decontamination apparatus 102 performs during the time period. Once the time period is over, signal analyzer 152 may reset the count. In some cases, the time period may correspond to the time between the instances in which decontamination apparatus 102 gets serviced (e.g., reviewed to make sure it is working properly, and adjustments are made to improve its performance). Consequently, signal analyzer 152 may ensure decontamination apparatus 102 continues to work properly in instances in which the number of decontamination cycles does not exceed a threshold but rather has been operating for a long period of time without any maintenance being performed.

In some embodiments, the counter may correspond to a moving window time period. Signal analyzer 152 may decrement the counter for the medical waste decontamination cycles that occurred outside of the moving window time period and increment the counter for each medical waste decontamination cycle that decontamination apparatus 102 performed within the time period. Signal analyzer 152 may compare the counter to a threshold to identify any instances in which decontamination apparatus 102 performed too many cycles within the moving window time period that could cause it to operate poorly (e.g., with multiple errors) for another cycle within the moving window time period. In such instances and when exceeding the threshold causes remote server 104 to send decontamination apparatus to send a signal preventing decontamination apparatus 102 from performing another medical waste decontamination cycle, signal analyzer 152 may determine when the counter decreases below the threshold and cause a signal to be sent to decontamination apparatus 102 that enables or indicates decontamination apparatus 102 can perform medical waste decontamination cycles again.

In some embodiments, signal analyzer 152 maintains counters for each type of medical waste decontamination cycle that decontamination apparatus 102 performs. To do so, for each medical waste decontamination cycle for which remote server 104 receives data, signal analyzer 152 may identify the type of the cycle from the data (e.g., an identification of the type) and increment the counter that corresponds to the identified type. Examples of types include, but are not limited to, Sharp and Red Bag. Signal analyzer 152 may maintain the counters for each type and compare the incremented counters to a threshold similar to the above. Each type may be associated with a different or the same threshold. Upon determining a counter for a type exceeds or satisfies a threshold, signal analyzer 152 may cause a signal to be transmitted to remote device 106 indicating the satisfied threshold and the type of cycle that is associated with the satisfied threshold. In some embodiments, signal analyzer 152 may identify a configuration from configuration database 160 that prevents decontamination apparatus 102 from performing a medical waste decontamination cycle associated with the type and cause the identified configuration to be transmitted to decontamination apparatus 102. The counters may be associated with time periods similar to the above. Consequently, signal analyzer 152 may ensure that decontamination apparatus 102 performs effective medical waste decontamination cycles for each cycle that it performs while avoiding the effects of degradation.

Signal selector 154 may comprise programmed instructions that, upon execution, cause processor 146 to select a signal to transmit to decontamination apparatus 102. Signal selector 154 may select the signals from configuration database 160. The signals that signal selector 154 selects may correspond to new configurations for decontamination apparatus 102. The signals may correspond to decontamination apparatus 102 performing medical waste decontamination cycles in the new configurations. Signal selector 154 may select the signals based on the signal that signal analyzer 152 identifies from configuration database 160 based on analyzing signals from medical waste decontamination cycles that remote server 104 receives from decontamination apparatus 102. Signal selector 154 may select the signals by retrieving them from configuration database 160.

Apparatus adjuster 156 may comprise programmed instructions that, upon execution, cause processor 146 to adjust operation of decontamination apparatus 102 by transmitting instructions comprising the signal that signal selector 154 selects to decontamination apparatus 102. Apparatus adjuster 156 may transmit the instructions to decontamination apparatus 102 via network interface 110 using the MQTT protocol to network interface 108 of decontamination apparatus 102. The signal may include a flag or setting of the selected signal that causes decontamination apparatus 102 to update its configuration for the next medical waste decontamination cycle that it performs.

Advantageously, by receiving signals for each medical waste decontamination cycle that decontamination apparatus performs, remote server 104 may remotely monitor decontamination apparatus 102 without polling decontamination apparatus 102 for data and ensure that decontamination apparatus 102 can adequately decontaminate medical waste while experiencing fewer errors. Remote server 104 may identify any degradation in performance (e.g., an increase in the number of errors that decontamination apparatus 102 experiences during medical waste decontamination cycles, an increase in the number of times decontamination apparatus 102 has to restart medical waste decontamination cycles before completing them, etc.) and adjust how decontamination apparatus 102 operates to improve its performance. Remote server 104 may perform the monitoring using a two-way communication protocol that maintains the privacy of any data that is generated by decontamination apparatus 102 by avoiding connecting to public networks (e.g., by using a cellular network) when communicating.

Referring still to FIG. 1, configuration manager 136 may comprise programmed instructions that, upon execution, cause processor 128 of decontamination apparatus 102 to facilitate communication between processes or modules of decontamination apparatus 102. Configuration manager 136 may be configured to receive signals from remote server 104 via network interface 108. Configuration manager 136 may identify the flag or setting of the signals that identifies the new configuration (e.g., the new firmware or new parameters) for decontamination apparatus 102. Configuration manager 136 may identify the new configuration and store the new configuration in memory 130, such as in cycle database 138 or another database. In some embodiments, configuration manager 136 may store the new configuration on a partition of the SD-card of decontamination apparatus 102 (e.g., as new parameters in the parameter file). Cycle controller 132 may access or retrieve the new parameters upon boot up or reboot of decontamination apparatus 102. In some embodiments, cycle controller 132 may access or retrieve the new configuration upon initiating a new medical waste decontamination cycle. Cycle controller 132 may perform the new medical waste decontamination cycle using the new configuration. Consequently, as referenced above, cycle controller 132 may perform the new medical waste decontamination cycle and future medical waste decontamination cycles in the new configuration with more accurate data utilization techniques (e.g., new methods of determining the temperature of chamber 120), while experiencing fewer errors, and while avoiding degradation of its performance. Each of these advantages can cause decontamination apparatus 102 to more effectively and consistently decontaminate medical waste.

In some embodiments, configuration manager 136 may identify the signal from remote server 104 to include a flag or setting of new firmware. Configuration manager 136 may update the firmware on decontamination apparatus 102 with the received new firmware. To do so, configuration manager 136 may identify the new firmware and determine whether cycle controller 132 is facilitating a medical waste decontamination cycle. Configuration manager 136 may do so by determining the current status of cycle controller 132. Responsive to determining cycle controller 132 is not facilitating a medical waste decontamination cycle, configuration manager 136 may initiate an upgrade of the firmware on decontamination apparatus 102. However, responsive to determining cycle controller 132 is facilitating a medical waste decontamination cycle, configuration manager 136 may transmit a signal to partitioner 140 indicating a new firmware update.

Partitioner 140 may comprise programmed instructions that, upon execution by processor 128, cause processor 128 to partition the processes being performed on decontamination apparatus 102 to allow for decontamination apparatus 102 to perform medical waste decontamination cycles while upgrading its firmware. Partitioner 140 may partition the processes into two sets of processes, cycle controller 132 may implement one set of processes to continue facilitating a medical waste decontamination cycle while partitioner 140 or configuration manager 136 upgrades the firmware to the new firmware using a second set of processes. Partitioner 140 or configuration manager 136 may upgrade the firmware using the second set of processes and, once both the firmware update is complete and cycle controller 132 has completed the respective medical waste decontamination cycle, configuration manager 136 can migrate the new firmware so cycle controller 132 and other components of processing circuit 112 can operate using the new firmware.

In some embodiments, configuration manager 136 may migrate the new firmware upon reboot or boot up of decontamination apparatus 102.

Advantageously, by partitioning the processes that decontamination apparatus 102 performs into two sets of processes, decontamination apparatus 102 may perform medical waste decontamination cycles without any downtime or a user needing to wait for the upgrade to complete. Thus, the decontamination apparatus 102 may perform bulk cycles without pausing for a firmware upgrade to complete.

In some embodiments, remote server 104 may be configured to enable users to remotely control how or when decontamination apparatus 102 performs medical waste decontamination cycles. For example, remote server 104 may generate a user interface at a client device that enables a user to remotely initiate or create settings for a medical waste decontamination cycle. Via the user interface, a user may input various settings such as delayed starts or set times that decontamination apparatus 102 performs cycles. Another example of a setting is a setting to cause decontamination apparatus 102 to initiate a medical waste decontamination cycle upon a lid of decontamination apparatus 102 latching or at a predetermined time after the lid latches. A user may also input changes to parameters of such cycles. The user may input any new settings or parameters at a user interface and transmit the new settings or parameters to remote server 104. Remote server 104 may transmit the new settings or parameters input by the user to decontamination apparatus 102 to adjust how or when decontamination apparatus 102 performs medical waste decontamination cycles.

In some embodiments, users may control decontamination apparatus 102 through a user account that is accessed through a user interface that is generated by remote server 104. The user account may be associated with a group identifier stored in a database of memory 148 of remote server 104. The group identifier may be associated with a particular medical facility and/or be associated with other user accounts. The group identifier may also be associated with a policy that sets how decontamination apparatus 102 performs medical waste decontamination cycles. Such a policy may enable decontamination apparatus 102 to perform medical waste decontamination cycles according to parameters that are specific to the facility, which may be advantageous if the facility typically attempts to decontaminate particular types of medical waste. The user may use their login credentials to access their user account and privileges associated with their user account to remotely adjust the configuration of decontamination apparatus 102.

Figure 2:
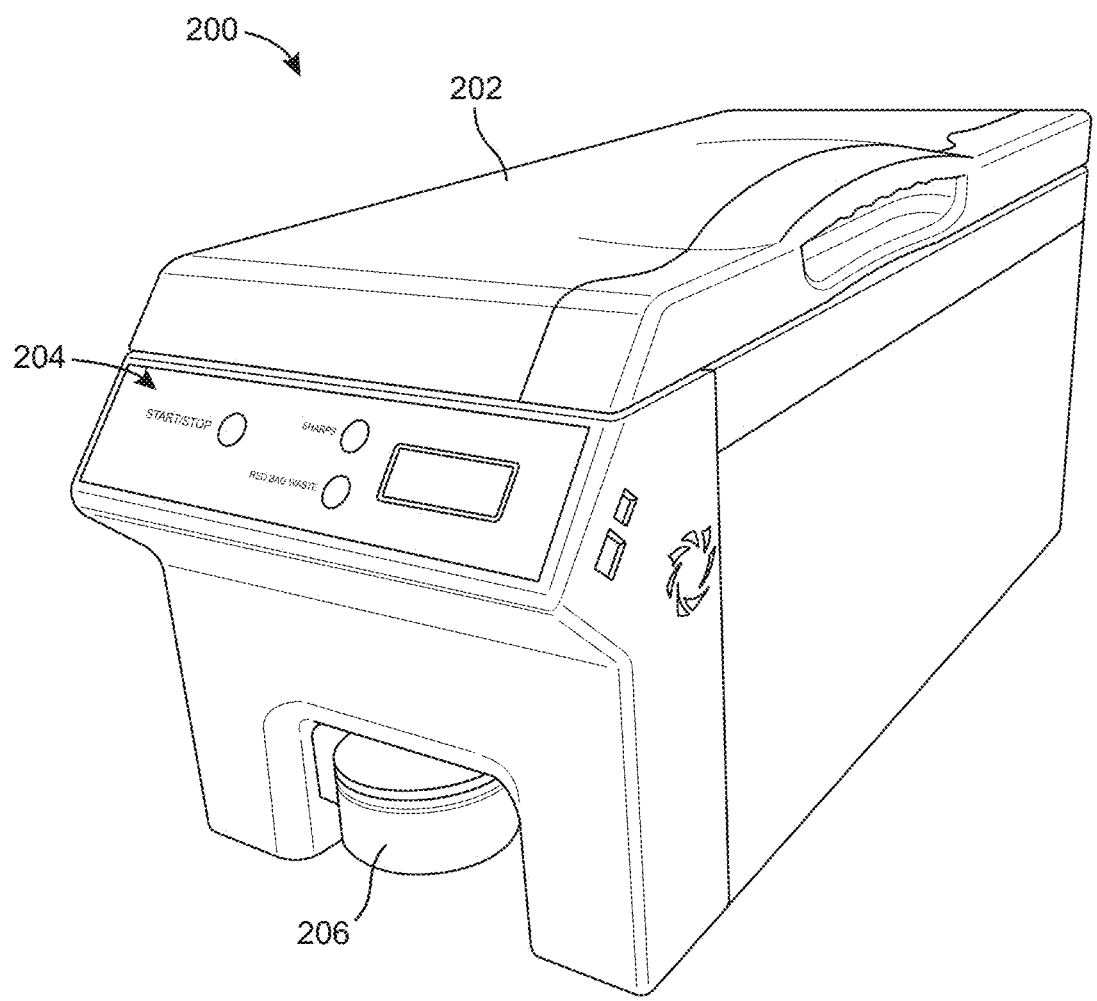
FIG. 2 is a perspective view of the decontamination apparatus of FIG. 1, in accordance with some embodiments of the present disclosure.

Referring now to FIG. 2, a perspective view of a decontamination apparatus 200 is shown, in accordance with some embodiments of the present disclosure. Decontamination apparatus 200 is shown to include a lid 202, a control dashboard 204, and a water extraction jar 206, in some embodiments. A user may open decontamination apparatus 200 by lifting a handle of lid 202. Decontamination apparatus 200 may perform medical waste decontamination cycles similar to decontamination apparatus 102, shown and described with reference to FIG. 1. To initiate medical waste decontamination cycles, a user may operate control dashboard 204 by selecting buttons indicating a type of waste that is being decontaminated and selecting a start input button. The user may stop a medical waste decontamination cycle by selecting a stop input button. Control dashboard 204 may include a display that shows the length of time left for the medical waste decontamination cycle.

While decontamination apparatus 200 performs the medical waste decontamination cycles, gas may build up as the waste is heated. Decontamination apparatus 200 may use a condenser (not shown) to convert the gas to liquid. The liquid of the gas may be transported and stored in water extraction jar 206.

Figure 3:
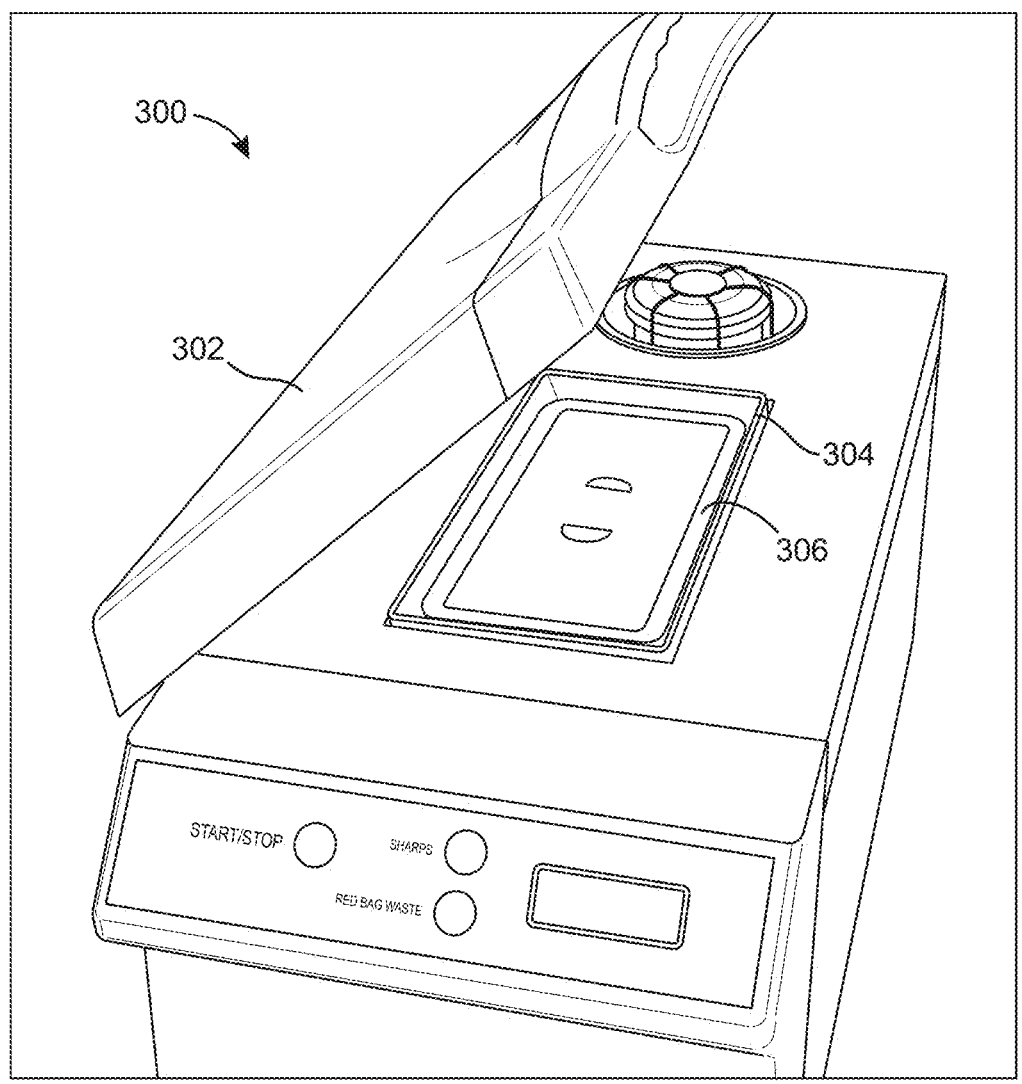
FIG. 3 is a perspective view of the decontamination apparatus of FIG. 1 with a lid open, in accordance with some embodiments of the present disclosure.

Referring now to FIG. 3, a perspective view of a decontamination apparatus 300 with a lid 302 open is shown, in accordance with some embodiments of the present disclosure. Decontamination apparatus 300 is shown to include lid 302, a chamber 304, and a container 306, in some embodiments. Decontamination apparatus 300 may perform medical waste decontamination cycles similar to decontamination apparatus 102, shown and described with reference to FIG. 1. A user may fill container 306 with medical waste such as Sharp or Red Bag waste and insert container 306 into chamber 304. The user may close lid 302 and initiate a medical waste decontamination cycle to decontaminate the waste within container 306.

Figure 4:
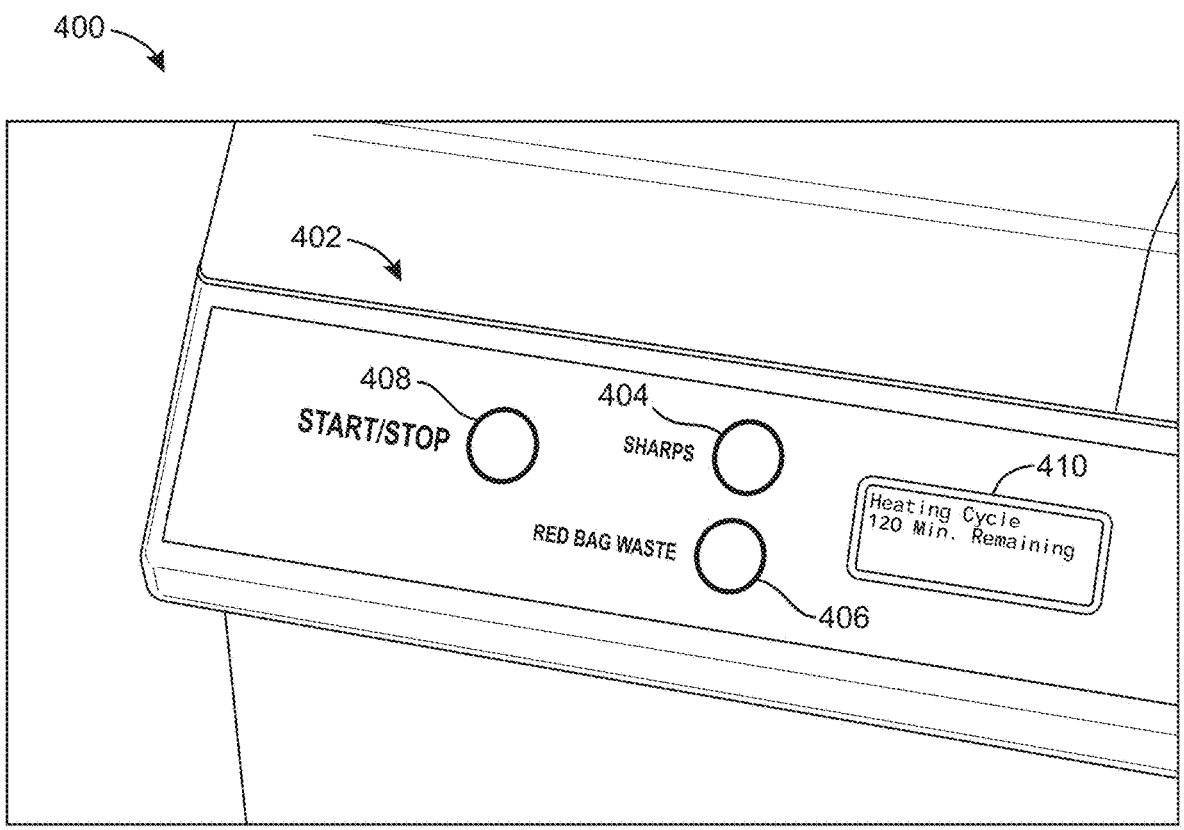
FIG. 4 is a front view of a user control panel of the decontamination apparatus of FIG. 1, in accordance with some embodiments of the present disclosure.

Referring now to FIG. 4, a front view of a user control panel 402 of a decontamination apparatus 400 is shown, in accordance with some embodiments of the present disclosure. Decontamination apparatus 400 may perform medical waste decontamination cycles similar to decontamination apparatus 102, shown and described with reference to FIG. 1. Via user control panel 402, a user may initiate a medical waste decontamination cycle to decontaminate medical waste. User control panel 402 is shown to include a Sharp button 404, a Red Bag Waste button 406, a start/stop button 408, and a display 410, in some embodiments. A user may initiate or stop a medical waste decontamination cycle by selecting one of Sharp button 404 or Red Bag Waste button 406 and selecting start/stop button 408. The user may view the time left for the medical waste decontamination cycle via display 410.

Figure 5:
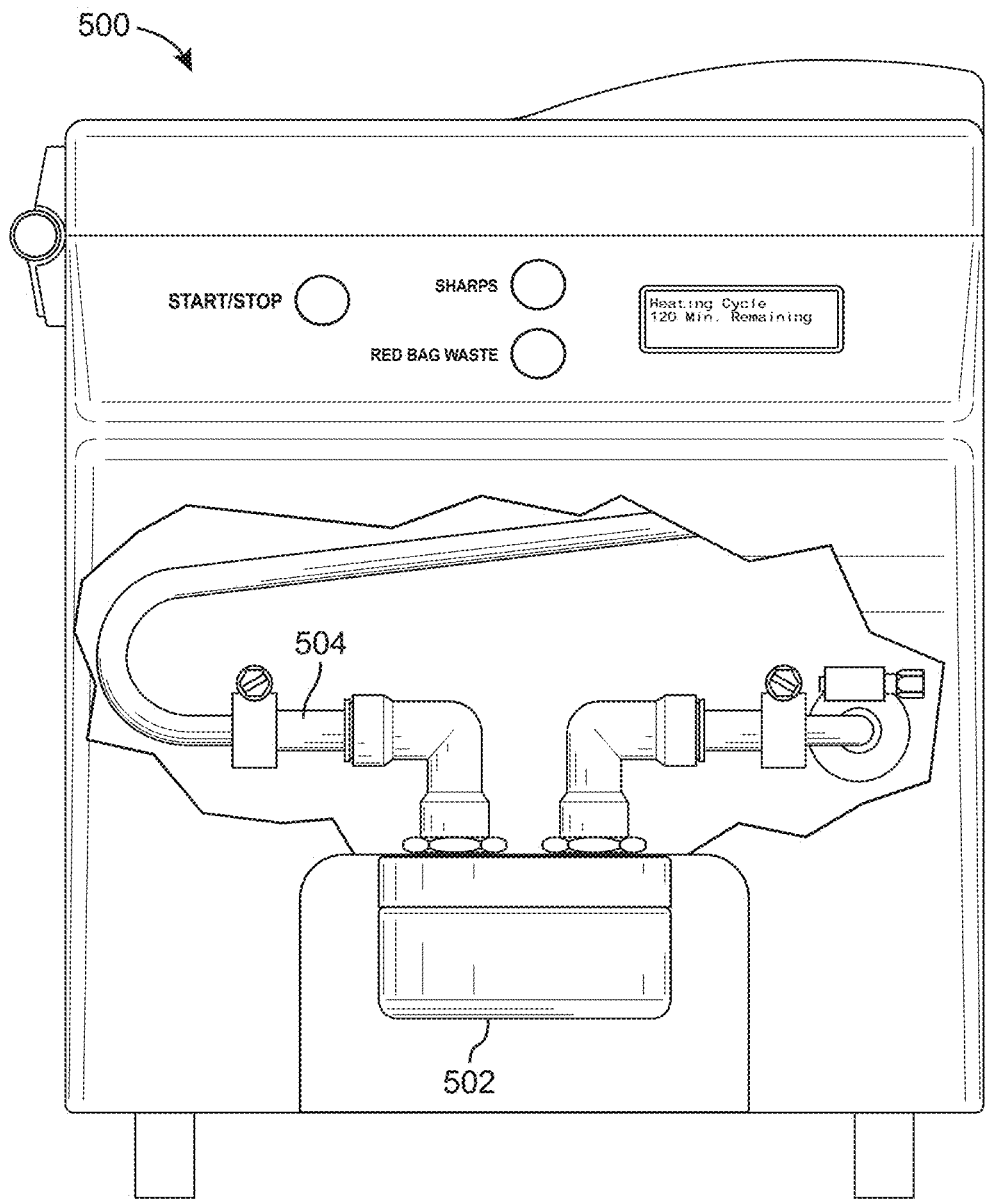
FIG. 5 is a front view of the mechanical components of the decontamination apparatus of FIG. 1, in accordance with some embodiments of the present disclosure.

Referring now to FIG. 5, a front view of the mechanical components of a decontamination apparatus 500 is shown, in accordance with some embodiments of the present disclosure. Decontamination apparatus 500 may perform medical waste decontamination cycles similar to decontamination apparatus 102, shown and described with reference to FIG. 1. Decontamination apparatus 500 is shown to include a water extraction jar 502 and a piping 504, in some embodiments. During a medical waste decontamination cycle, gas and/or liquid that passes through a condenser (not shown) may pass through piping 504 and go into water extraction jar 502.

Figure 6:
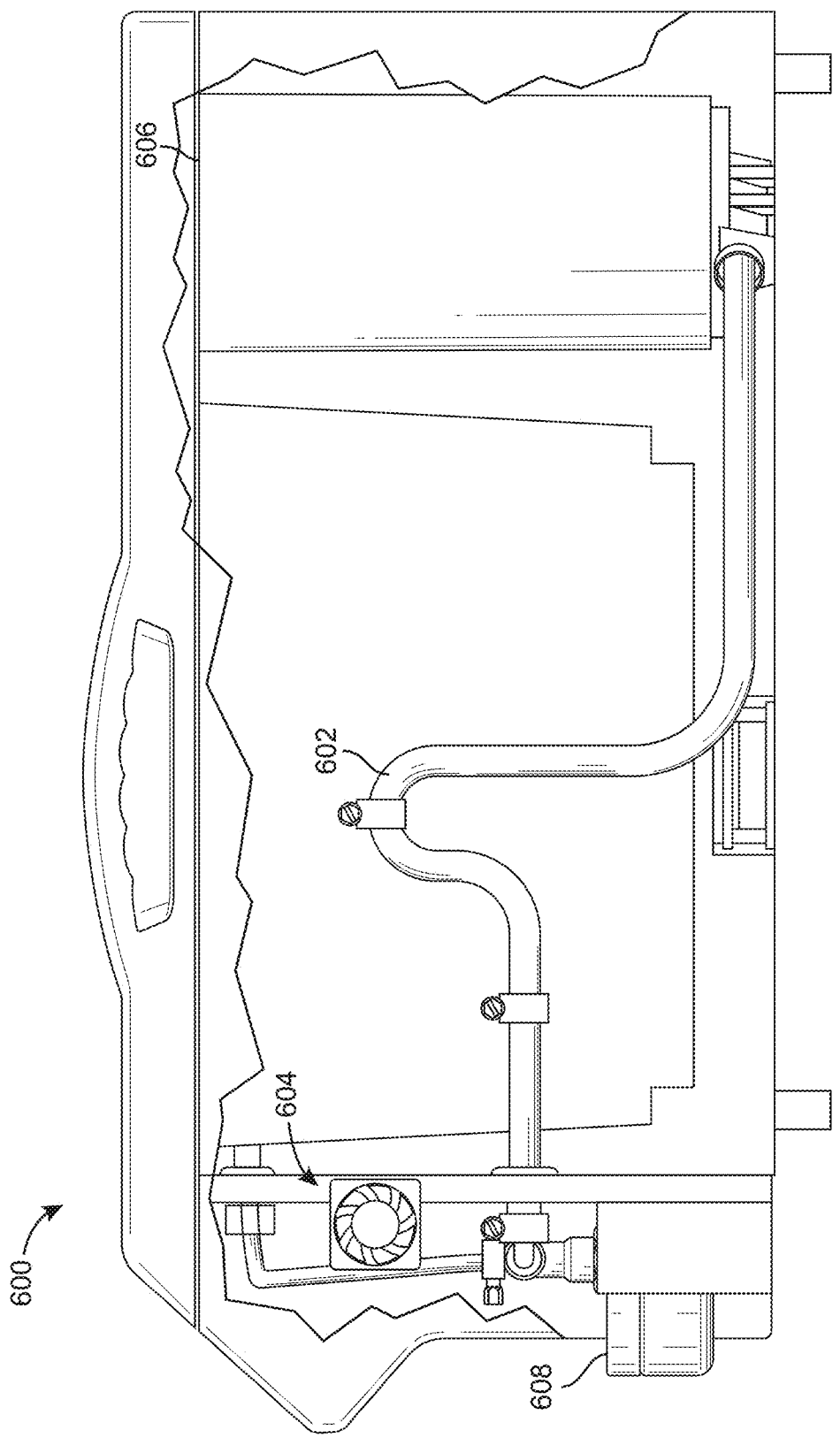
FIG. 6 is a side view of the mechanical components of the decontamination apparatus of FIG. 1, in accordance with some embodiments of the present disclosure.

Referring now to FIG. 6, a side view of the mechanical components of a decontamination apparatus 600 of FIG. 1 is shown, in accordance with some embodiments of the present disclosure. Decontamination apparatus 600 may perform medical waste decontamination cycles similar to decontamination apparatus 102, shown and described with reference to FIG. 1. Decontamination apparatus 600 is shown to include piping 602, a fan 604, a condenser 606, and a water extraction jar 608, in some embodiments. During a medical waste decontamination cycle, gas may pass through condenser 606 and through piping 602 to go into water extraction jar 608. Fan 604 may be configured to cause air pulled in from the bottom of decontamination apparatus 600 to leave the housing of decontamination apparatus 600.

Figure 7:
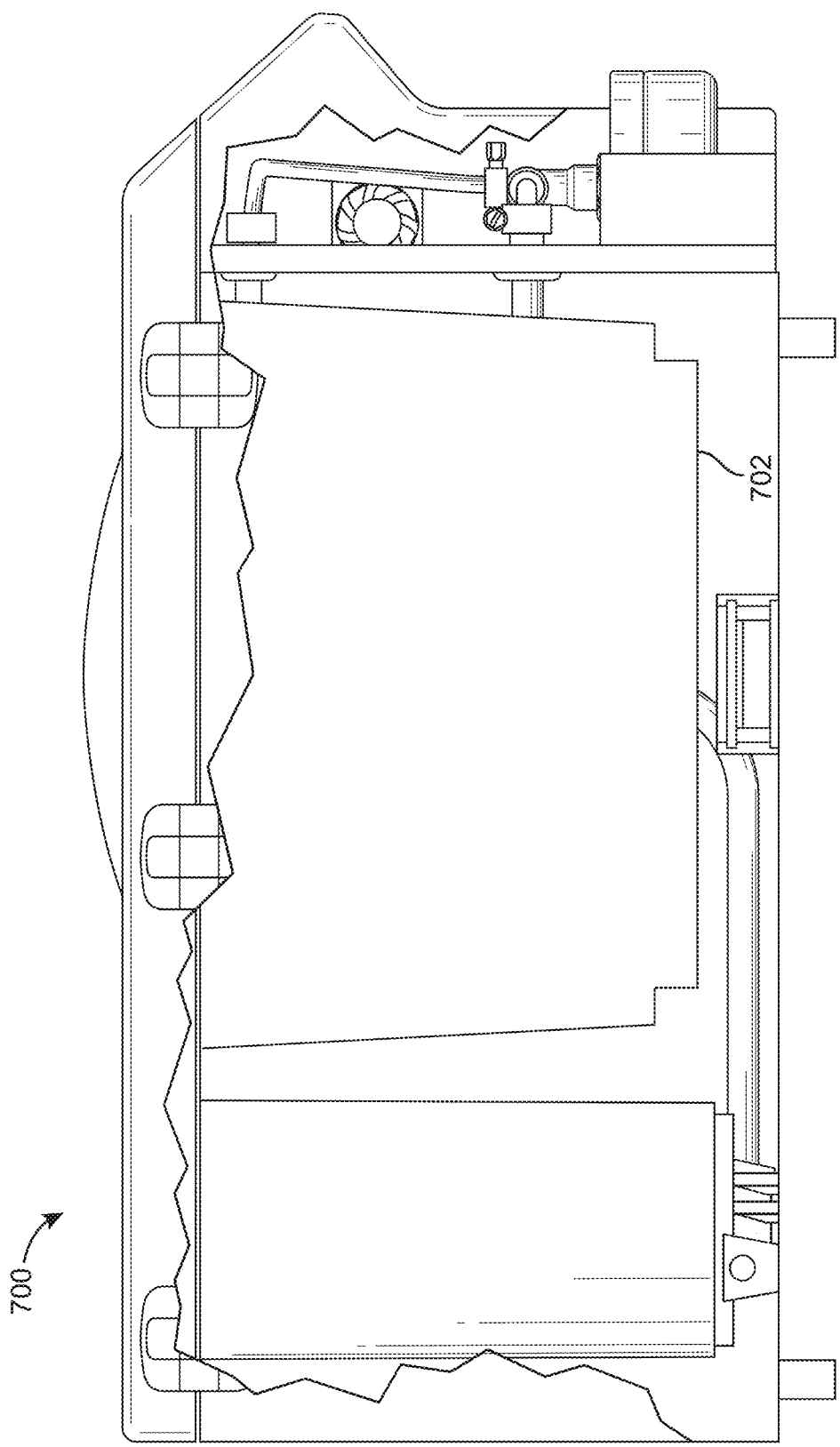
FIG. 7 is another side view of the mechanical components of the decontamination apparatus of FIG. 1, in accordance with some embodiments of the present disclosure.

Referring now to FIG. 7, another side view of the mechanical components of a decontamination apparatus 700 is shown, in accordance with some embodiments of the present disclosure. Decontamination apparatus 700 may perform medical waste decontamination cycles similar to decontamination apparatus 102, shown and described with reference to FIG. 1. Decontamination apparatus 700 is shown to include a chamber 702, in some embodiments. As described herein, medical waste may be placed into chamber 702 and heated. The medical waste may be heated into bricks filled with plastic (e.g., plastic from syringe containers) so they may be disposed of.

Figure 8:
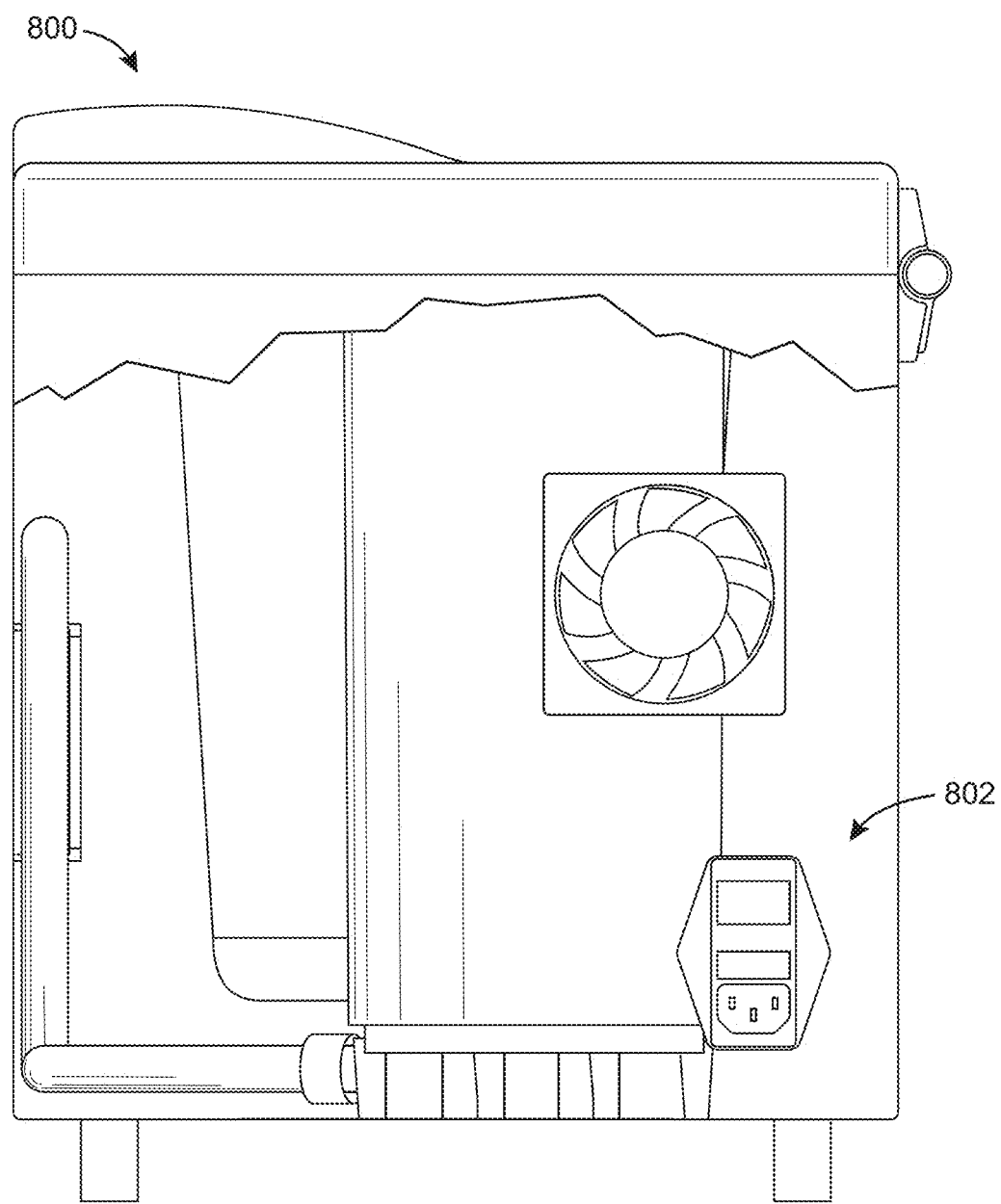
FIG. 8 is a back view of the mechanical components of the decontamination apparatus of FIG. 1, in accordance with some embodiments of the present disclosure.

Referring now to FIG. 8, a back view of the mechanical components of a decontamination apparatus 800 is shown, in accordance with some embodiments of the present disclosure. Decontamination apparatus 800 may perform medical waste decontamination cycles similar to decontamination apparatus 102, shown and described with reference to FIG. 1. Decontamination apparatus 800 is shown to include a power outlet 802, in some embodiments. Decontamination apparatus 800 may be powered by being plugged into the wall via power outlet 802.

Figure 9:
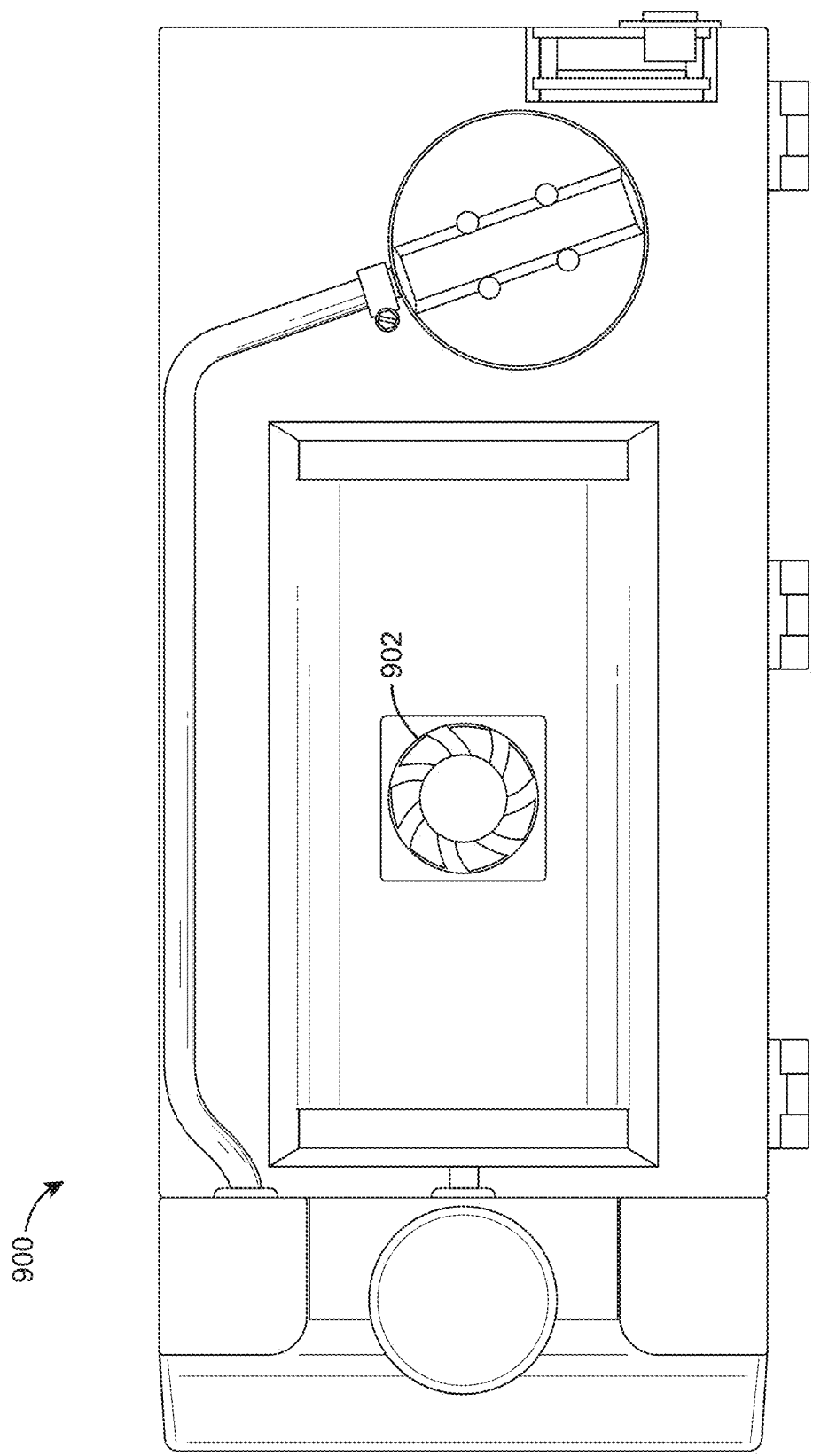
FIG. 9 is a bottom view of the mechanical components of the decontamination apparatus of FIG. 1, in accordance with some embodiments of the present disclosure.

Referring now to FIG. 9, a bottom view of the mechanical components of a decontamination apparatus 900 is shown, in accordance with some embodiments of the present disclosure. Decontamination apparatus 900 may perform medical waste decontamination cycles similar to decontamination apparatus 102, shown and described with reference to FIG. 1. Decontamination apparatus 900 is shown to include a fan 902, in some embodiments. Fan 902 may be configured to bring in cool air from below decontamination apparatus 900 during a medical waste decontamination cycle to cool the circuitry of the unit and/or a chamber of decontamination apparatus 900 during a cool-down period of the cycle.

Figure 10:
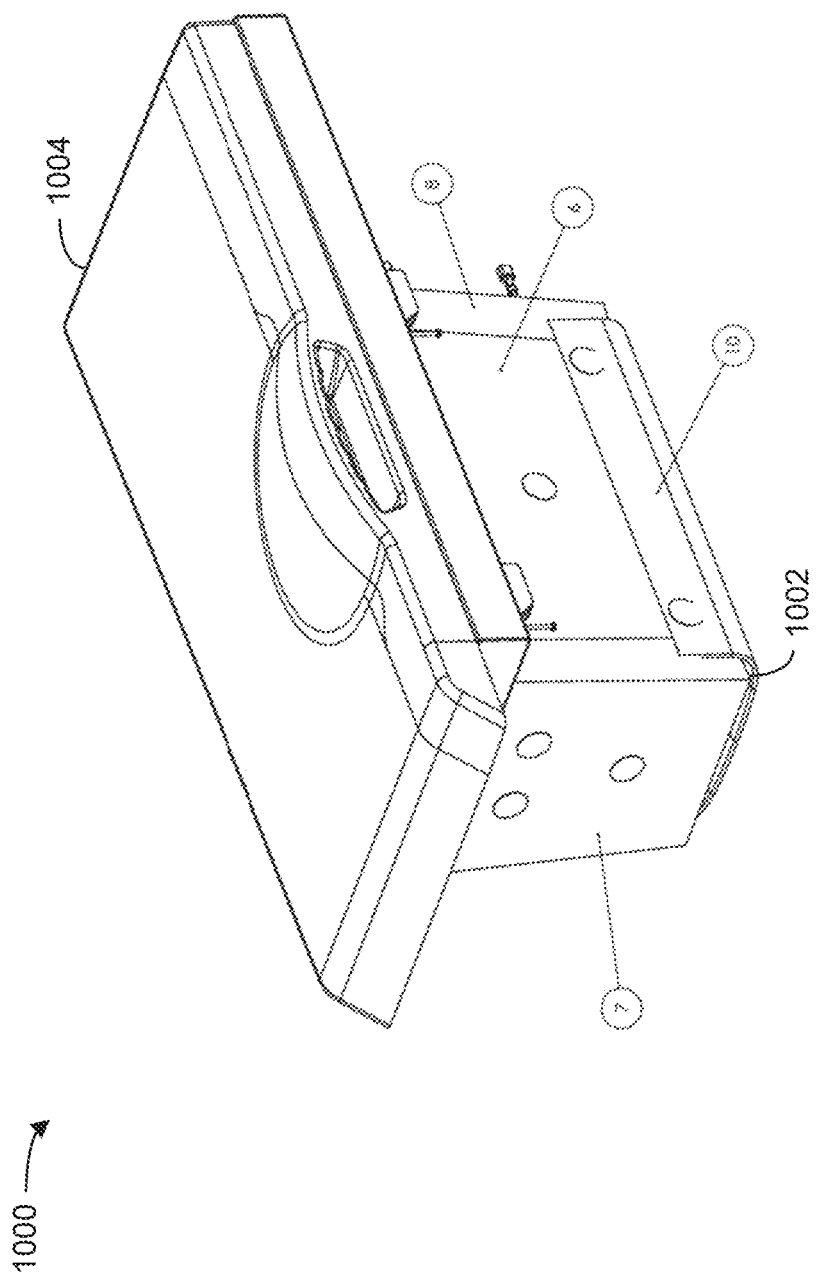
FIG. 10 is a perspective view of a chamber and a lid of the decontamination apparatus of FIG. 1, in accordance with some embodiments of the present disclosure.

Referring now to FIG. 10, a perspective view of a chamber 1002 and a lid 1004 of a decontamination apparatus 1020 is shown, in accordance with some embodiments of the present disclosure. Decontamination apparatus 1020 may perform medical waste decontamination cycles similar to decontamination apparatus 102, shown and described with reference to FIG. 1. As described herein, waste may be decontaminated within chamber 1002. Chamber 1002 may be enclosed by lid 1004 to stop gases from leaving the unit and users from opening the unit during a medical waste decontamination cycle.

Figure 11:
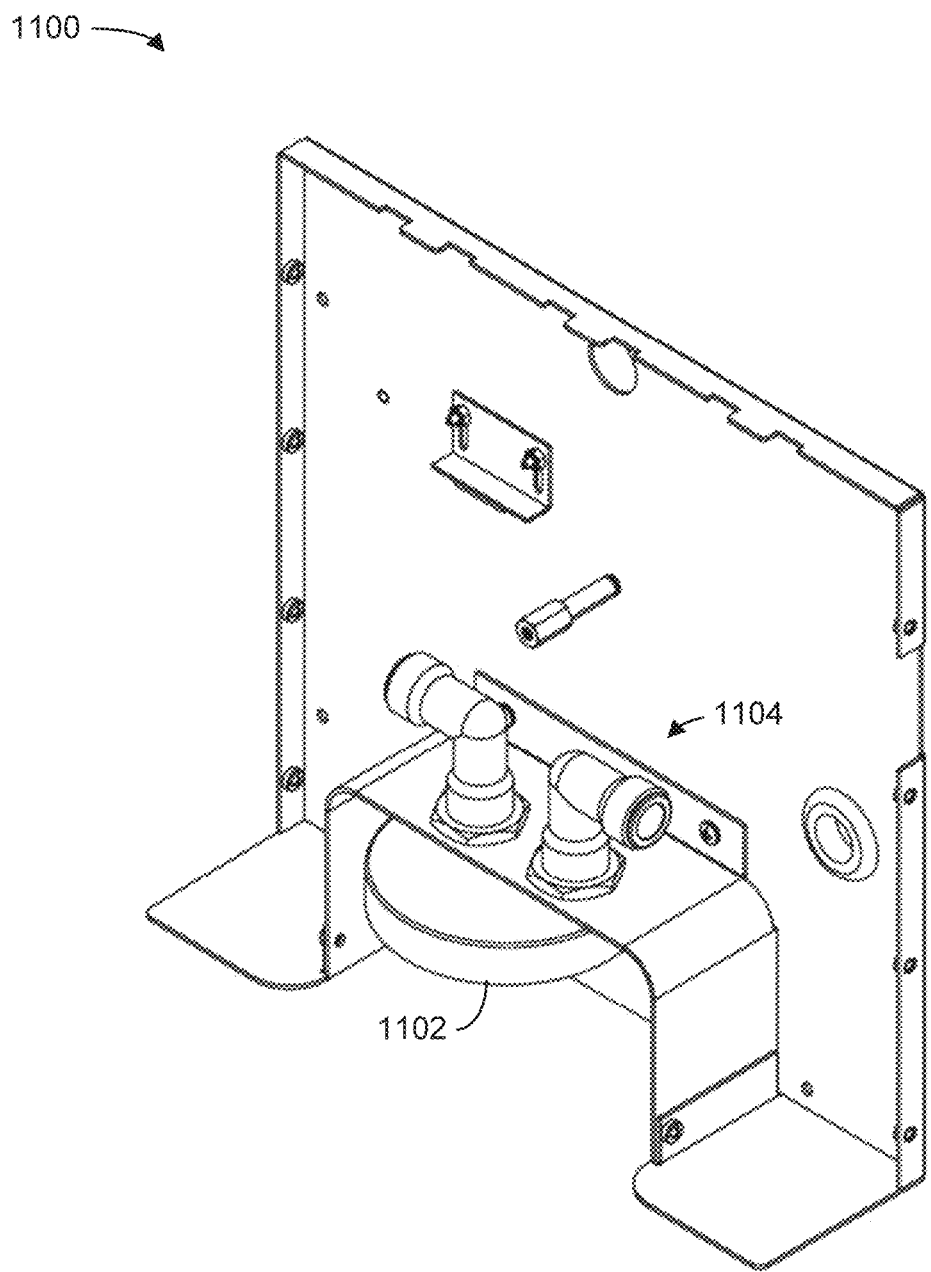
FIG. 11 is a perspective view of the mechanical components of the front of the decontamination apparatus of FIG. 1, in accordance with some embodiments of the present disclosure.

Referring now to FIG. 11, a perspective view of the mechanical components of the front of a decontamination apparatus 1100 is shown, in accordance with some embodiments of the present disclosure. Decontamination apparatus 1020 may perform medical waste decontamination cycles similar to decontamination apparatus 102, shown and described with reference to FIG. 1. Decontamination apparatus 1100 is shown to include a water extraction jar 1102 and a piping coupler system 1104, in some embodiments. Piping coupler system 1104 may include two piping couplers that couple to piping that facilitates the flow of gas and/or liquids from a condenser into water extraction jar 1102.

Figure 12A:
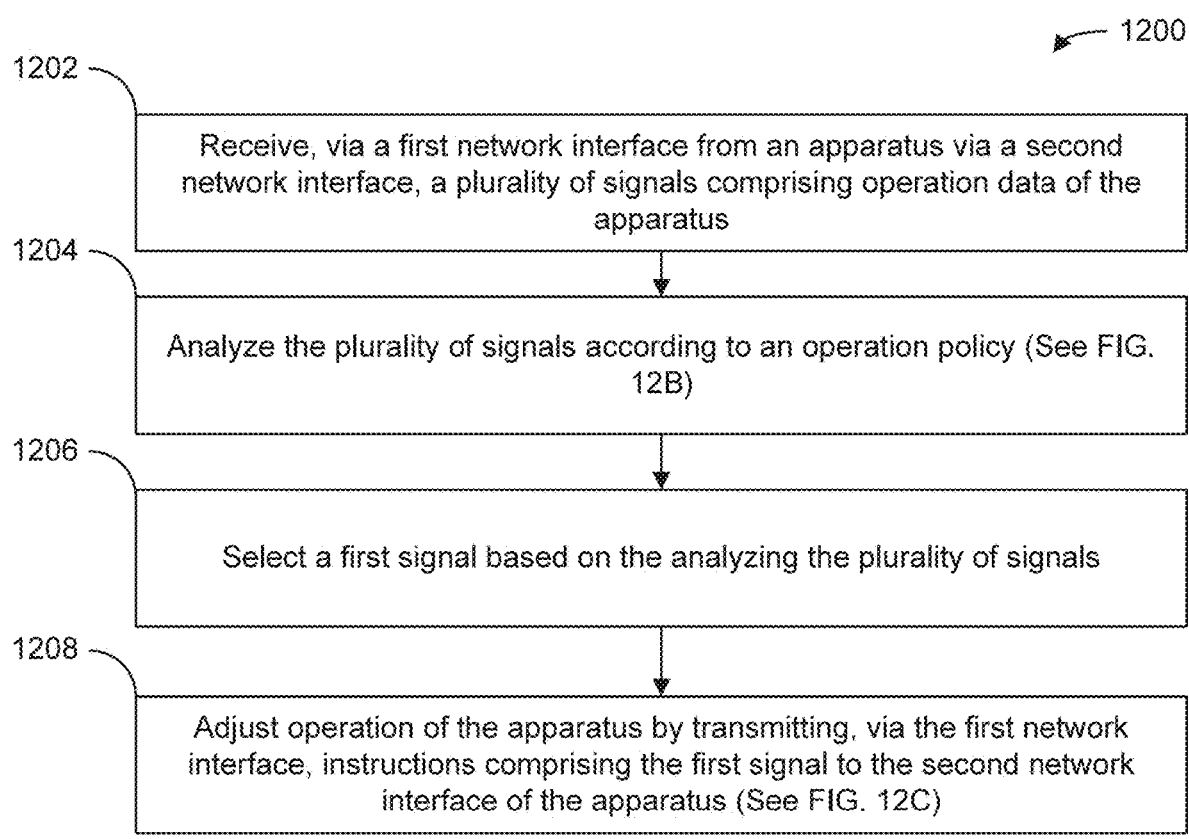
FIG. 12A is an example flowchart for a method for remote control of decontamination of medical waste in the decontamination apparatus of FIG. 1, in accordance with some embodiments of the present disclosure.

Referring now to FIG. 12A, an example flowchart for a method 1200 for remote control of decontamination of medical waste in a decontamination apparatus is shown, in accordance with some embodiments of the present disclosure. Performance of method 1200 enables a remote monitoring server to monitor how a decontamination apparatus, such as the decontamination apparatus described herein, operates over time to identify errors that occur and any degradations in performance of the decontamination apparatus. The remote monitoring server may receive data about the configuration of the decontamination apparatus as it performs such medical waste decontamination cycles and data about the cycles themselves (e.g., the temperature at different points in time, the number of errors that occurred, the errors that occurred, etc.). The remote monitoring server may analyze the data and determine whether there is a configuration for the decontamination apparatus to resolve the errors or degradations. Upon identifying such a configuration, the remote monitoring server may transmit the configuration to the decontamination apparatus, causing the decontamination apparatus to operate more efficiently (e.g., experience fewer errors that cause restarts to cycles), consistently, and effectively.

At operation 1202, the remote monitoring server may receive, via a first network interface from a decontamination apparatus via a second network interface, a plurality of signals comprising operation data of the decontamination apparatus. The first network interface may be a cellular network interface, Ethernet, or Wi-Fi. The remote monitoring server may receive the signals in data packets via a MQTT protocol. The data packets may comprise byte strings. The operation data of the decontamination apparatus may comprise signals and errors generated during a medical waste decontamination cycle and configuration data of the decontamination apparatus when it performed the cycle. Examples of operation data can include an identification of the firmware operating on the decontamination apparatus, the international mobile equipment identity (IMEI) of the decontamination apparatus, cell network strength, the IP address of the decontamination apparatus, the minimum and maximum temperature achieved during the medical waste decontamination cycle, the length of the medical waste decontamination cycle, the number of times the medical waste decontamination cycle restarted, the time the medical waste decontamination cycle started, the time the medical waste decontamination cycle ended, the type of the decontamination cycle, etc. In some embodiments, the operation data may additionally include a type of waste that the decontamination apparatus decontaminated during the cycle. The remote monitoring server may receive a signal at each instance the decontamination apparatus performs a medical waste decontamination cycle and store the data of each signal.

At operation 1204, the remote monitoring server may analyze the plurality of signals according to an operation policy. How the remote monitoring server analyzes the plurality of signals is explained further below with respect to FIG. 12B.

At operation 1206, the remote monitoring server may select a first signal based on analyzing the plurality of signals. The first signal may include new configuration data to send to the decontamination apparatus. The remote monitoring server may select the first signal based on the outcome of analyzing the plurality of signals according to an operation policy. For example, the remote monitoring server may select the first signal after determining that the decontamination apparatus is experiencing more errors than usual (e.g., averaging more errors across a group of recent medical waste decontamination cycles than across its lifetime or what is expected by an amount above a threshold). The remote monitoring server may identify and select a new configuration (e.g., new parameters) for the decontamination apparatus as a first signal.

At operation 1208, the remote monitoring server may adjust operation of the decontamination apparatus by transmitting, via the first network interface, instructions comprising the first signal to the second network interface of the decontamination apparatus. The remote monitoring server may use the same network interface (e.g., a cellular network interface) to transmit the selected configuration data to the decontamination apparatus that the decontamination apparatus used to transmit the plurality of signals comprising operation data. By transmitting the first signal comprising configuration data to the decontamination apparatus, the remote monitoring server may cause the decontamination apparatus to operate the next cycle and, in some cases, future cycles under the new configuration. Such operation under the new configuration may allow the decontamination apparatus to operate more efficiently, effectively, and experience fewer errors as it performs future medical waste decontamination cycles. Operation 1208 is described in more detail below with respect to FIG. 12C.

Figure 12B:
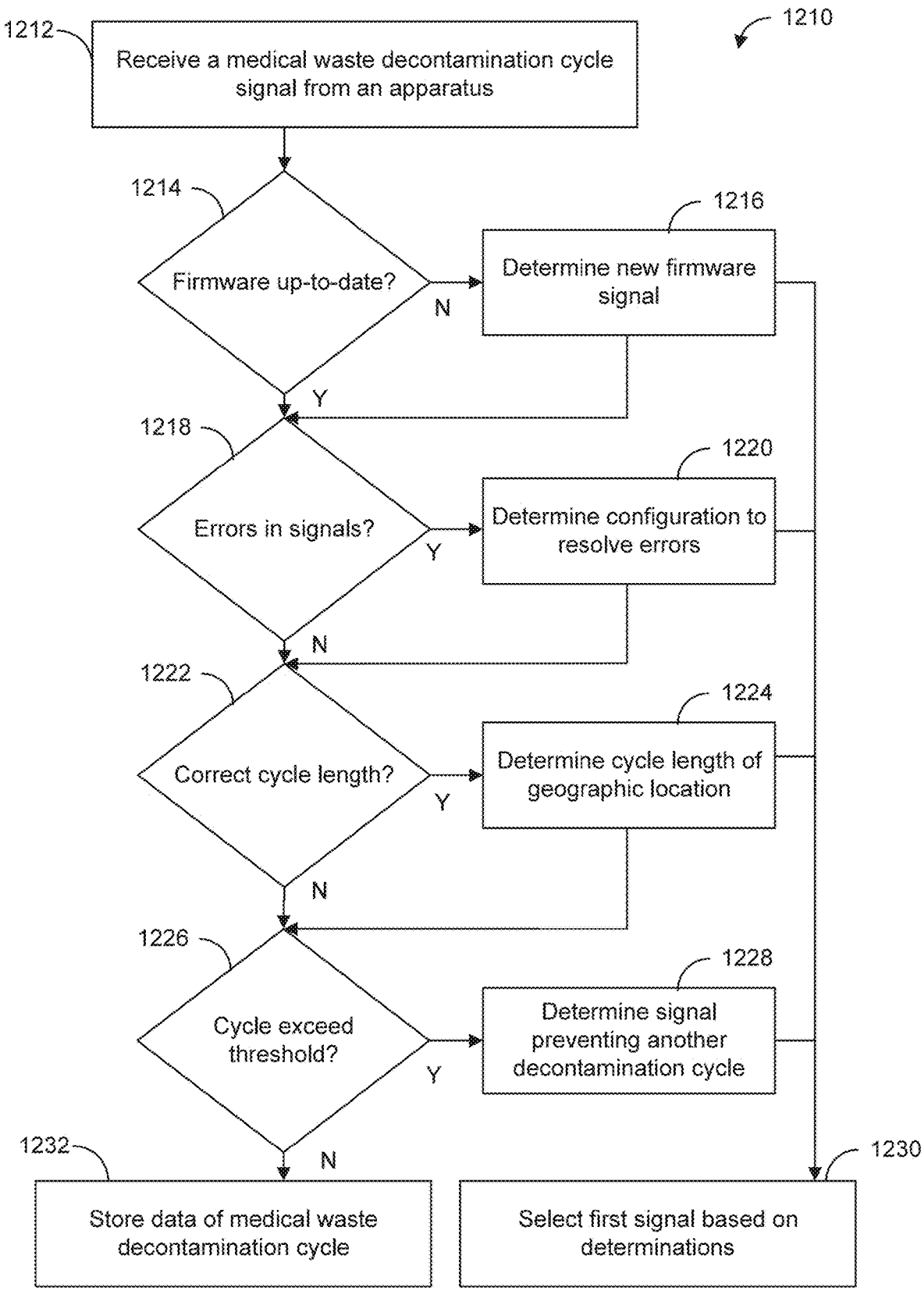
FIG. 12B is an example flowchart for analyzing decontamination cycle signals received from the apparatus of FIG. 1, in accordance with some embodiments of the present disclosure.

Referring now to FIG. 12B, an example flowchart for a method 1210 for analyzing decontamination cycle signals received from an decontamination apparatus is shown, in accordance with some embodiments of the present disclosure. Method 1210 may be performed by a remote monitoring server or any other device in communication with the decontamination apparatus over a network interface. Method 1210 may correspond to operation 1204, shown and described with reference to FIG. 12A. At operation 1212, the remote monitoring server may receive a medical waste decontamination cycle signal from the decontamination apparatus. The medical waste decontamination cycle signal may comprise operation data of the decontamination apparatus as it performed a medical waste decontamination cycle. At operation 1214, the remote monitoring server may determine if the firmware of the decontamination apparatus is up-to-date. The remote monitoring server may do so by comparing an identification of the firmware from the operation data to firmware stored in a database of the remote monitoring server. Responsive to determining there is a more recent version of the firmware operating on the decontamination apparatus, at operation 1216, the remote monitoring server may determine a new signal (e.g., generate a signal comprising the new firmware for install) to send to the decontamination apparatus.

After determining the new signal comprising the new firmware, or responsive to determining the firmware on the decontamination apparatus is up-to-date, at operation 1218, the remote monitoring server may determine whether there were any errors in the signal (e.g., any errors that occurred during the medical waste decontamination cycle). The remote monitoring server may do so by identifying any errors from the data packet of the medical waste decontamination cycle. Responsive to the remote monitoring server identifying at least one error, at operation 1220, the remote monitoring server may determine a configuration to resolve the error so it does not occur in a future medical waste decontamination cycle. The remote monitoring server may do so by comparing the error or set of errors to a set of pattern-decontamination cycle configuration pairs stored in a database of the remote monitoring server. The remote monitoring server may identify a pattern-decontamination cycle configuration pair that matches the error or errors from the signal and the corresponding configuration to determine the configuration to resolve the errors and prevent them from occurring in future cycles.

In some embodiments, the remote monitoring server may identify a new configuration for the decontamination apparatus after identifying a spike in the number or type of errors that occur in the decontamination apparatus. For example, the remote monitoring server may determine that it is normal for the decontamination apparatus to experience an error every five medical waste decontamination cycles. However, the remote monitoring server may maintain a counter for the number of errors that occur across cycles and determine that the decontamination apparatus is experiencing at least one error every cycle. The remote monitoring server may make such a determination by comparing the number of errors of a moving window time period to a threshold. Responsive to determining the number of errors exceed a threshold, the remote monitoring server may identify the degradation in the performance of the decontamination apparatus and the types and/or number of errors that are occurring. The remote monitoring server may compare the types and/or number of errors to the database to identify a configuration of a pattern-decontamination cycle configuration pair that matches the types and/or number of errors. In some embodiments, the remote monitoring server may compare the errors to the pattern-decontamination cycle configuration pairs of the database and identify any matching pairs and the corresponding configuration to send to the decontamination apparatus.

After determining the new signal comprising the new configuration to resolve the errors and/or the degradation of the decontamination apparatus, or responsive to determining no errors occurred for a medical waste decontamination cycle, at operation 1222, the remote monitoring server may determine whether the decontamination apparatus performed the medical waste decontamination cycle with the correct cycle length. The correct cycle length may correspond to the geographic location in which the decontamination apparatus performed the medical waste decontamination cycle. For example, different geographical regions may have different requirements for the length of a hold period of a medical waste decontamination cycle. The remote server may store the cycles that correspond to each geographic location in a database of the remote server. The remote server may identify the location of the decontamination apparatus using the IP address of the signal it receives from the decontamination apparatus or based on a relationship table within the remote monitoring server that identifies the entity that controls the decontamination apparatus and the location of the entity. Responsive to determining the location of the decontamination apparatus, the remote server may compare the location to the database to determine the cycle length that corresponds to the location. Responsive to determining the cycle length was not correct based on the location of the decontamination apparatus, at operation 1224, the remote monitoring server may select a signal with the correct cycle length.

After determining the new signal comprising the new cycle length to resolve the errors, or responsive to determining the cycle length was correct, at operation 1226, the remote monitoring server may determine whether the decontamination apparatus has performed a number of cycles that exceed a threshold. For each medical waste decontamination cycle for which the remote monitoring server receives data, the remote monitoring server may increment a counter. The remote monitoring server may compare the counter to a threshold to determine if the decontamination apparatus has performed enough medical waste decontamination cycles to satisfy or exceed the threshold. In some embodiments, the remote monitoring server may identify a type of the cycle from the signal and increment a counter corresponding to the type. The remote monitoring server may determine when the decontamination apparatus has performed enough medical waste decontamination cycles to exceed a threshold that corresponds to the type.

Responsive to determining the decontamination apparatus has performed enough medical waste decontamination cycles to exceed a threshold, at operation 1228, the remote monitoring server may determine a signal that prevents another decontamination cycle. The remote monitoring server may do so by identifying a new configuration from a database of the remote monitoring server that corresponds to the decontamination apparatus performing enough cycles to satisfy the threshold. The signal may cause the decontamination apparatus to be unable or stop the decontamination apparatus from performing future medical waste decontamination cycles. In cases in which the threshold corresponds to a specific type of cycle, the signal may only stop the decontamination apparatus from performing cycles specific to the corresponding type.

In some embodiments, instead of or in addition to determining and/or sending a signal that prevents the decontamination apparatus from performing another cycle, the remote monitoring server may transmit a signal to a third device indicating the threshold has been met or satisfied. The signal may be shown on a user interface of the third device.

After determining the signals and/or new configurations to send to the decontamination apparatus in operations 1216, 1220, 1224, and/or 1228, when applicable, the remote monitoring server may select the signals from the database or databases of the remote monitoring server. The remote monitoring server may transmit each of the applicable signals back to the decontamination apparatus to adjust its operation.

After determining the new signal comprising the new configuration to prevent the decontamination apparatus from performing another cycle, or responsive to determining the threshold was not satisfied, at operation 1232, the remote monitoring server may store the operation data of the medical waste decontamination cycle. The remote decontamination cycle may store the operation data in a database of the remote monitoring server.

Figure 12C:
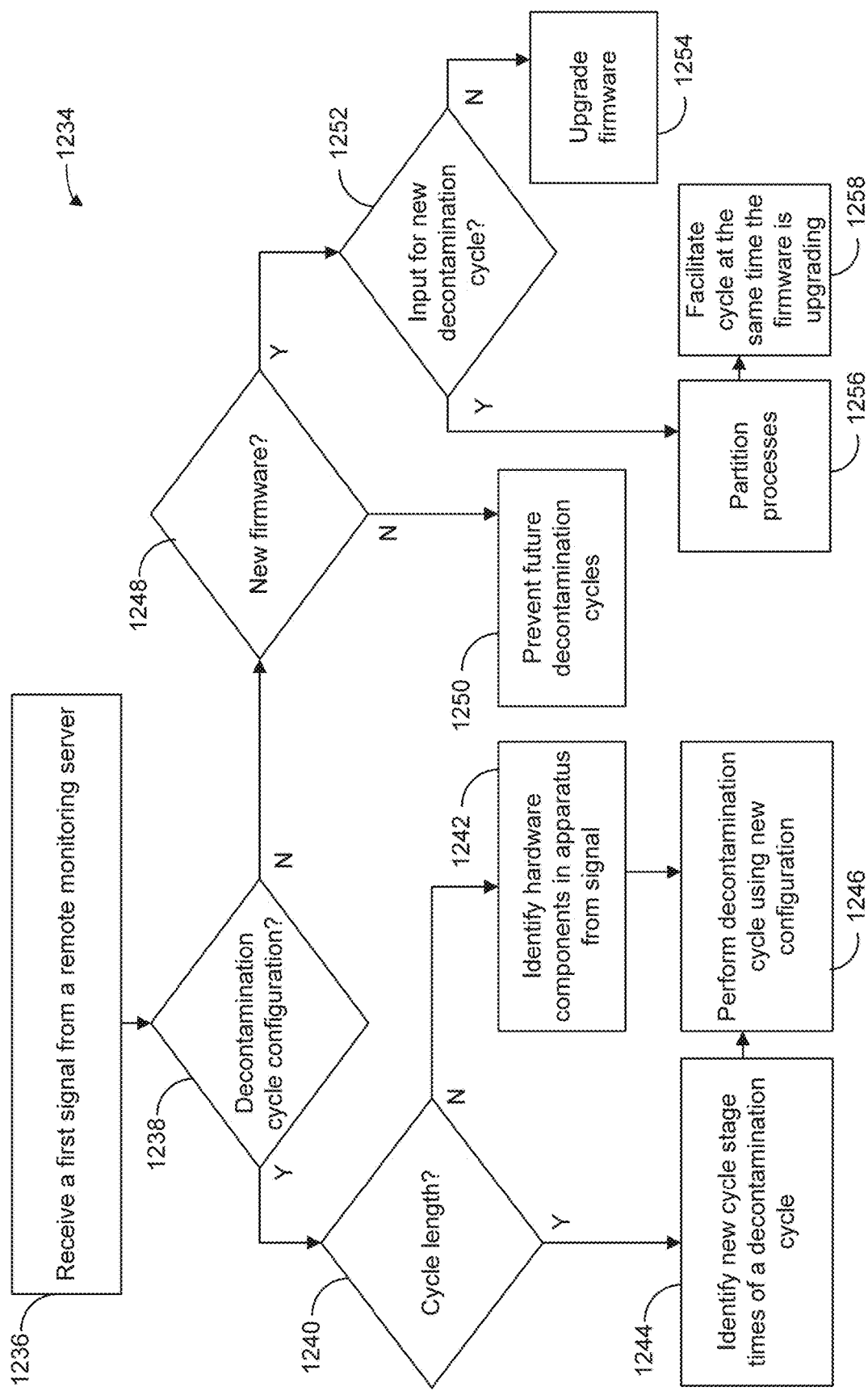
FIG. 12C is an example flowchart for adjusting operation of the apparatus of FIG. 1 based on analyzing the decontamination cycle signals, in accordance with some embodiments of the present disclosure.

Referring now to FIG. 12C, an example flowchart for a method 1234 for adjusting operation of a decontamination apparatus based on analyzing decontamination cycle signals is shown, in accordance with some embodiments of the present disclosure. Method 1234 may be performed by the decontamination apparatus or any other device in communication with a remote monitoring server over a network interface. Method 1234 may correspond to operation 1208, shown and described with reference to FIG. 12B. At operation 1236, the decontamination apparatus may receive a first signal from a remote server. The decontamination apparatus may receive the first signal after sending the remote monitoring server operation data of the decontamination apparatus when it performed a medical waste decontamination cycle and the remote monitoring server analyzed the operation data. The first signal may comprise configuration data of the decontamination apparatus. The configuration data may comprise various flags or settings, such as new firmware or new parameters to use that, upon being implemented, cause the decontamination apparatus to perform medical waste decontamination cycles in a new configuration.

At operation 1238, the decontamination apparatus may determine whether the first signal is associated with a decontamination cycle configuration. An example of a decontamination cycle configuration may include a length of a period of the cycle or different methods of determining errors or the temperature within the chamber of the decontamination apparatus during the cycle. The decontamination apparatus may determine whether the first signal is associated with a decontamination cycle configuration based on the flag or setting identifying the new configuration of the decontamination apparatus. Responsive to determining the first signal comprises a new decontamination cycle configuration at operation 1240, the decontamination apparatus may determine if the new decontamination cycle configuration is a new cycle length (e.g., a new hold period of a cycle).

Responsive to determining the new configuration is associated with a new cycle length, at operation 1244, the decontamination apparatus may identify the new cycle length and adjust its internal control strategy so the next medical waste decontamination cycle that the decontamination apparatus performs has the new cycle length. Responsive to determining the new configuration is not associated with cycle length, at operation 1242, the decontamination apparatus may identify the hardware components of the new configuration. The hardware components may be the temperature sensors that generate data indicating the temperature within the chamber of the decontamination apparatus. The new configuration may cause the decontamination apparatus to adjust its control strategy to determine the temperature of the chamber using a different combination of the sensors, such as adjusting from taking an average of each of the temperature sensors to using the sensor with the highest or lowest value, or vice versa. The decontamination apparatus may store the changes of operations 1242 and/or 1244 upon receipt to be implemented for the next medical waste decontamination cycle. At operation 1246, the decontamination apparatus may perform such a cycle using the stored configuration of operations 1242 and/or 1244.

Responsive to determining the first signal does not comprise or contain decontamination cycle configuration data at operation 1238, at operation 1248, the decontamination apparatus may determine if the configuration data comprises new firmware. Responsive to determining the first signal does not comprise new firmware, at operation 1250, the decontamination apparatus may determine the signal comprises configuration data that prevents the decontamination apparatus from performing future medical waste decontamination cycles. Consequently, when a user presses an input button to attempt to initiate a medical waste decontamination cycle, the decontamination apparatus may generate a message at a display indicating the cycle cannot be performed. In cases in which the signal indicates the type of cycle that cannot be performed, the decontamination apparatus may only generate the message for the specific type of cycle.

However, responsive to determining that the first signal comprises new configuration data, at operation 1252, the decontamination apparatus may determine whether an input has been received that initiated a medical waste decontamination cycle or whether such a cycle is currently ongoing. Responsive to determining such an input has not been received or that a cycle is not ongoing, at operation 1254, the decontamination apparatus may upgrade the firmware of its circuitry. However, responsive to determining such an input has been received or that a cycle is ongoing, at operation 1256, the decontamination apparatus may partition the processes that it performs into multiple sets of processes. For example, the decontamination apparatus may partition the processes that use current or old firmware perform into a first set of processes and the processes that are upgrading the current or old firmware to the new firmware into a second set of processes. At operation 1258, the decontamination apparatus may perform the initiated medical waste decontamination cycle using the current firmware in the first set of processes while the decontamination apparatus upgrades the old or current firmware using the second set of processes. Consequently, the decontamination apparatus may upgrade its firmware without a waiting period.

The various illustrative logical blocks, modules, circuits, and algorithm operations described in connection with the examples disclosed herein may be implemented as electronic hardware, computer software, or combinations of both. To clearly illustrate this interchangeability of hardware and software, various illustrative components, blocks, modules, circuits, and operations have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present disclosure.

The hardware used to implement the various illustrative logics, logical blocks, modules, and circuits described in connection with the examples disclosed herein may be implemented or performed with a general purpose processor, a DSP, an ASIC, an FPGA or other programmable logic device, discrete gate or transistor logic, discrete hardware components, or any combination thereof designed to perform the functions described herein. A general-purpose processor may be a microprocessor, but, in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration. Alternatively, some operations or methods may be performed by circuitry that is specific to a given function.

In some exemplary examples, the functions described may be implemented in hardware, software, firmware, or any combination thereof. If implemented in software, the functions may be stored as one or more instructions or code on a non-transitory computer-readable storage medium or non-transitory processor-readable storage medium. The operations of a method or algorithm disclosed herein may be embodied in a processor-executable software module which may reside on a non-transitory computer-readable or processor-readable storage medium. Non-transitory computer-readable or processor-readable storage media may be any storage media that may be accessed by a computer or a processor. For example but not limitation, such non-transitory computer-readable or processor-readable storage media may include RAM, ROM, EEPROM, FLASH memory, CD-ROM or other optical disk storage, magnetic disk storage or other magnetic storage devices, or any other medium that may be used to store desired program code in the form of instructions or data structures and that may be accessed by a computer. Disk and disc, as used herein, includes compact disc (CD), laser disc, optical disc, digital versatile disc (DVD), floppy disk, and blu-ray disc where disks usually reproduce data magnetically, while discs reproduce data optically with lasers. Combinations of the above are also included within the scope of non-transitory computer-readable and processor-readable media. Additionally, the operations of a method or algorithm may reside as one or any combination or set of codes and/or instructions on a non-transitory processor-readable storage medium and/or computer-readable storage medium, which may be incorporated into a computer program product.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components and/or wirelessly interactable and/or wirelessly interacting components and/or logically interacting and/or logically interactable components.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances, where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B." Further, unless otherwise noted, the use of the words "approximate," "about," "around," "substantially," etc., mean plus or minus ten percent.

The foregoing description of illustrative embodiments has been presented for purposes of illustration and of description. It is not intended to be exhaustive or limiting with respect to the precise form disclosed, and modifications and variations are possible in light of the above teachings or may be acquired from practice of the disclosed embodiments. It is intended that the scope of the invention be defined by the claims appended hereto and their equivalents.

What is claimed is:

1. A method for remote control of decontamination of medical waste in an apparatus, the method comprising:
receiving, by a server via a first network interface and from the apparatus via a second network interface, a plurality of signals, the plurality of signals comprising operation data of the apparatus generated while the apparatus performs medical waste decontamination cycles in a first configuration;
analyzing, by the server, the plurality of signals according to an operation policy;
selecting, by the server, a first signal based on the analyzing the plurality of signals; and
adjusting, by the server, operation of the apparatus by transmitting, via the first network interface, instructions to the second network interface of the apparatus, the instructions comprising the first signal,
wherein receipt of the instructions causes the apparatus to perform a medical waste decontamination cycle in a second configuration different from the first configuration.

2. The method of claim 1, wherein the first network interface and the second network interface are cellular network interfaces.

3. The method of claim 1, wherein the plurality of signals comprise indications of each medical waste decontamination cycle that the apparatus performs, the method further comprising:
for each indication of a medical waste decontamination cycle that the server receives:
incrementing, by the server, a count of a counter indicating the number of medical waste decontamination cycles the apparatus has performed;
comparing, by the server, the incremented count to a threshold; and
responsive to the incremented count satisfying the threshold, transmitting, by the server, an alert to a first device indicating the apparatus performed a number of medical waste decontamination cycles that satisfies the threshold.

4. The method of claim 1, wherein the apparatus performs a first type of medical waste decontamination cycle and a second type of medical waste decontamination cycle, and wherein the plurality of signals comprise indications of each medical waste decontamination cycle that the apparatus performs and associated indications of the types of each of the medical waste decontamination cycles, the method further comprising:
maintaining, by the server, counters for the first type of medical waste decontamination cycle and the second type of medical waste decontamination cycle; and
for each indication of a medical waste decontamination cycle that the server receives:
identifying, by the server, the type of the medical waste decontamination cycle from the associated indication of the type of medical waste decontamination cycle;
incrementing, by the server, a count of a counter indicating the number of medical waste decontamination cycles the apparatus has performed for the identified type of medical waste decontamination cycle;
comparing, by the server, the incremented count to a threshold, the threshold corresponding to the identified type; and
responsive to the incremented count satisfying the threshold, transmitting, by the server, an alert to a first device indicating the apparatus performed a number of medical waste decontamination cycles that satisfies the threshold.

5. The method of claim 1, wherein the operation data comprises error data associated with errors that occurred during the medical waste decontamination cycles, wherein analyzing the plurality of signals according to the operation policy comprises:
comparing, by the server, the error data to a set of pattern-decontamination cycle configuration pairs stored in a database, each of the pattern-decontamination cycle configuration pairs comprising error data and a corresponding decontamination cycle configuration; and
matching, by the server, the error data to a pattern-decontamination cycle configuration pair,
wherein the first signal comprises the decontamination cycle configuration of the matched pattern-decontamination cycle configuration pair.

6. The method of claim 1, wherein the plurality of signals comprise an indication of a current firmware configuration of the apparatus, the method further comprising:
comparing, by the server, the current firmware configuration of the apparatus to a database; and
based on the comparison, determining, by the server, there is a new firmware configuration stored in the database, wherein the first signal comprises the new firmware configuration.

7. The method of claim 6, wherein the apparatus further comprises a processor, and wherein transmission of the instructions comprising the first signal to the second network interface of the apparatus causes the processor to:
partition processes that the processor performs into a first set of processes and a second set of processes,
wherein the processor updates the current firmware configuration of the apparatus to the new firmware configuration of the apparatus using the first set of processes at the same time that the processor facilitates the medical waste decontamination cycle using the second set of processes.

8. The method of claim 1, wherein the apparatus comprises a heating element and a fan, and wherein the second configuration of the apparatus comprises a different heating element configuration and a different fan configuration than a heating element configuration and fan configuration of the first configuration of the apparatus.

9. The method of claim 1, wherein the plurality of signals further comprise geographical location data of the apparatus, and wherein, the first configuration of the apparatus comprises a first cycle length and the second configuration of the apparatus comprises a second cycle length different from the first cycle length, the method further comprising:
    comparing, by the server, the geographical location data to a database, the database storing associations between the first cycle length and one or more first locations and associations between the second cycle length and one or more second locations, and
        wherein selecting the first signal comprises:
            identifying, by the server, a match between the geographical location data and the stored one or more second locations, and
            selecting, by the server, the second cycle length based on the identified match, the first signal comprising the selected second cycle length.

10. The method of claim 9, wherein each medical waste decontamination cycle comprises a ramp-up period in which a chamber of the apparatus holding medical waste heats up, a hold period in which the chamber remains at a substantially constant temperature, and a cool-down period in which the temperature of the chamber cools down, and wherein the difference between the first cycle length and the second cycle length comprises a difference between the hold periods of the first cycle length and the second cycle length.

11. The method of claim 1, wherein the apparatus comprises a processor that facilitates medical waste decontamination cycles, a chamber, and a plurality of thermistors configured to determine the temperature within the chamber, and wherein when the apparatus performs a medical waste decontamination cycle in the first configuration, the processor determines the temperature within the chamber based on an average temperature of the plurality of thermistors, and when the apparatus performs a medical waste decontamination cycle in the second configuration, the processor determines the temperature within the chamber based on a temperature reading from only one thermistor of the plurality of thermistors.

12. A method for remote control of decontamination of medical waste in an apparatus, the method comprising:
    transmitting, by the apparatus via a first network interface and to a server via a second network interface, a plurality of signals, the plurality of signals comprising operation data of the apparatus generated while the apparatus performs medical waste decontamination cycles in a first configuration, transmission of the plurality of signals causing the server to:
        analyze the plurality of signals according to an operation policy;
        select a first signal based on the analyzing the plurality of signals; and
        adjust operation of the apparatus by transmitting, via the second network interface, instructions to the first network interface of the apparatus, the instructions comprising the first signal; and
    responsive to receiving the instructions comprising the first signal, performing a medical waste decontamination cycle in a second configuration different from the first configuration.

13. The method of claim 12, further comprising:
facilitating, by the apparatus, a first medical waste decontamination cycle;
responsive to the medical waste decontamination cycle ending, repeatedly transmitting, by the apparatus via the first network interface to the server via the second network interface, data of the first medical waste decontamination cycle;
receiving, by the apparatus via the first network interface, an indication that the server has completed processing the data;
responsive to receiving the indication, stopping transmission of the data and deleting, by the apparatus, the data of the first medical waste decontamination cycle from memory.

14. The method of claim 13, wherein the apparatus comprises a heating element and a fan, and wherein the second configuration of the apparatus comprises a different heating element configuration and a different fan configuration than a heating element configuration and fan configuration of the first configuration of the apparatus.

15. The method of claim 12, further comprising:
responsive to facilitating a first medical waste decontamination cycle, transmitting, by the apparatus via the first network interface, a signal to the server indicating current configuration characteristics of the apparatus, the current configuration characteristics comprising current firmware configuration information of the apparatus,
    wherein receipt of the current configuration characteristics of the apparatus causes the server to identify a new firmware configuration from a database and transmit the new firmware configuration to the apparatus;
receiving, by the apparatus, the new firmware configuration;
responsive to receiving the new firmware configuration, updating the current firmware configuration of the apparatus using a first set of processes partitioned from a second set of processes;
receiving, by the apparatus and via a push button of the apparatus, a user input to perform a second medical waste decontamination cycle; and
responsive to receiving the user input, facilitating, by the apparatus, the second medical waste decontamination cycle using the second set of processes at the same time that the apparatus updates the current firmware configuration of the apparatus using the first set of processes.

\* \* \* \* \*